US010155054B2

(12) United States Patent
Lafaye et al.

(10) Patent No.: US 10,155,054 B2
(45) Date of Patent: Dec. 18, 2018

(54) VARIABLE DOMAINS OF CAMELID HEAVY-CHAIN ANTIBODIES DIRECTED AGAINST GLIAL FIBRILLARY ACIDIC PROTEINS

(71) Applicants: INSTITUT PASTEUR, Paris (FR); CENTRE NATIONAL DE LA RECHERCHE SCIENTIFIQUE (CNRS), Paris (FR)

(72) Inventors: Pierre Lafaye, Malakoff (FR); Jean-Pierre Bourgeois, Saint Mande (FR); Francois Rougeon, Sevres (FR)

(73) Assignees: INSTITUT PASTEUR, Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 15/442,794

(22) Filed: Feb. 27, 2017

(65) Prior Publication Data

US 2017/0165383 A1 Jun. 15, 2017

Related U.S. Application Data

(60) Division of application No. 13/889,668, filed on May 8, 2013, now abandoned, which is a continuation of application No. 13/002,910, filed as application No. PCT/IB2009/006596 on Jul. 10, 2009, now Pat. No. 8,460,888.

(30) Foreign Application Priority Data

Jul. 10, 2008 (EP) ..................... 08290683

(51) Int. Cl.
*C07K 16/18* (2006.01)
*A61K 47/68* (2017.01)
*A61K 51/10* (2006.01)
*C07K 16/30* (2006.01)
*C12N 5/079* (2010.01)
*A61K 39/00* (2006.01)

(52) U.S. Cl.
CPC .......... *A61K 51/1018* (2013.01); *C07K 16/18* (2013.01); *C07K 16/3053* (2013.01); *C12N 5/0622* (2013.01); *A61K 2039/505* (2013.01); *A61K 2039/54* (2013.01); *A61K 2039/543* (2013.01); *A61K 2039/545* (2013.01); *C07K 2317/22* (2013.01); *C07K 2317/569* (2013.01); *C07K 2317/92* (2013.01)

(58) Field of Classification Search
CPC .......... C07K 2317/22; C07K 2317/569; C07K 2317/92; A61K 51/1018; A61K 47/6803; A61K 47/6843
See application file for complete search history.

(56) References Cited

U.S. PATENT DOCUMENTS

| 5,004,697 A | 4/1991 | Pardridge et al. |
| 6,027,887 A | 2/2000 | Zavada et al. |
| 8,460,888 B2 | 6/2013 | Lafaye et al. |
| 2006/0240480 A1 | 10/2006 | Curdt et al. |
| 2008/0107601 A1* | 5/2008 | Lauwereys ............ C07K 16/28 424/9.1 |
| 2009/0047300 A1 | 2/2009 | Abulrob et al. |
| 2010/0021384 A1 | 1/2010 | Rougeon et al. |
| 2011/0171720 A1 | 7/2011 | Muruganandam et al. |
| 2014/0206081 A1 | 7/2014 | Lafaye et al. |

FOREIGN PATENT DOCUMENTS

| EP | 2008666 A1 * | 12/2008 | ......... A61K 51/1018 |
| EP | 2009445 A1 * | 12/2008 | ......... C07K 14/4711 |
| WO | 2002/057445 A1 | 7/2002 | |
| WO | 2004/044204 A2 | 5/2004 | |
| WO | 2007/036021 A1 | 4/2007 | |
| WO | 2008/013934 A2 | 1/2008 | |
| WO | 2008/049897 A1 | 5/2008 | |

OTHER PUBLICATIONS

LaFerla FM et al. Intracellular amyloid-beta in Alzheimer's disease. Nat. Rev. Neuroscience, 2007, 8:499-509. (Year: 2007).*
Machine translation for WO 2004/044204 A2, from EPO patent Translate, retrieved Jul. 2014. (Year: 2014).*
Wikipedia entry for "Isoelectric point", retrieved Mar. 13, 2018. (Year: 2018).*
Chekhonin et al., PEGylated immunoliposomes directed against brain astrocytes. Drug Delivery, 12:1-6. (2005).
Pardridge, "Drug and Gene Delivery to the Brain: The Vascular Route," Neuron, vol. 36, pp. 555-558, Nov. 14, 2002.
Tamai et al., "Drug delivery through the blood-brain barrier," Advanced Drug Delivery Reviews, vol. 19, Issue 3, pp. 401-424, 1996 (Abstract).
Abulrob et al., "Single domain antibodies as blood-brain barrier delivery vectors," International Congress Series, vol 1277, pp. 212-223, 2005 (Abstract).
Office Action issued by the Examiner in application No. 12/501,094 dated Oct. 13, 2011.
Office Action issued by the Examiner in application No. 12/501,094 dated Jun. 17, 2011.
International Search Report issued for application No. PCT/IB2009/006596 dated Oct. 30, 2009.
Reeves et al., "Molecular cloning and primary structure of human glial fibrillary acidic protein," Proc. Natl. Acad. Sci. USA, vol. 86, pp. 5178-5182, Jul. 1989.

(Continued)

*Primary Examiner* — Kimberly Ballard
(74) *Attorney, Agent, or Firm* — Arrigo, Lee, Guttmann & Mouta-Bellum LLP

(57) ABSTRACT

The present invention relates to the use of variable domains of camelid heavy-chain antibodies (VHH domains) directed against an intracellular target and having an isoelectric point of at least 8.5, for targeting said intracellular target or for the preparation of a peptide vector. Particularly, it concerns VHH domains directed against a glial fibrillary acidic protein and uses thereof for preparing therapeutic or diagnostic agents.

14 Claims, 17 Drawing Sheets
Specification includes a Sequence Listing.

(56) References Cited

OTHER PUBLICATIONS

Abulrob et al., "The blood-brain barrier transmigrating single domain antibody: mechanisms of transport and antigenic epitopes in human brain endothelial cells," Journal of Neurochemistry, vol. 95, , pp. 1201-1214, 2005.
Muruganandam et al., "Selection of phage-displayed llama single-domain antibodies that transmigrate across the human blood-brain barrier endothelium," The FASEB Journal, vol. 16, pp. 240-242, Feb. 2002.
Van Der Linden et al., "Comparison of physical chemical properties of llama VHH antibody fragments and mouse monoclonal antibodies," Biochim. Biophys. Acta., vol. 1431, pp. 37-46, 1999.
Office Action issued in U.S. Appl. No. 13/002,910 dated Feb. 28, 2012.
Office Action issued in U.S. Appl. No. 13/002,910 dated Jun. 15, 2012.
Notice of Allowance issued in U.S. Appl. No. 13/002,910 dated Feb. 7, 2013.
Office Action issued in U.S. Appl. No. 13/889,668 dated Jun. 30, 2016.

* cited by examiner

```
VHH-E3      DVQLQVSGGGSVQPGGSLRLSCAAPGFTFSNYAMYWLRQAPGKGIEWVSRIGPGGSHTEY
VHH-B8      DVQLQVSGGGSVQPGGSLRLSCAAPGFTFSNYAMYWLRQAPGKGIEWVSRIGPGGSHTEY
VHH-E9      DVQLQVSGGGSVQPGGSLRLSCAASGFTFSNYAMYWLRQAPGKGIEWVSRIGPGGSHTEY
VHH-A10     DVQLRASGGGLVQPGGSLRLSCAASGFTFSNYAMYWLRQAPGKGIEWVSRIGPGGSHTEY
            ****:.******************.**********************************

VHH-E3      ADSVKGRFAISRDNAKNTLSLQMNSLKPEDTAAYYCAITQQGSGRGRGTQVTVSSAAA--
VHH-B8      ADSVKGRFAISRDNAKNTLSLQMNSLKPEDTAAYYCAITQQGSGRGRGTQVTVSSAAASL
VHH-E9      ADSVKGRFTISRDNAKNTLSLQMNSLKPEDTAVYYCAITQQGSGRGQGTQVTVSSAAA-
VHH-A10     ADSVKGRFTISRDNAKNTLSLQMNSLKPEDTAVYYCAITQQGSGRGQETQVTVSSAAA--
            ********:***********************.*************: **********

VHH-E3      ------------------------------------------------------------
VHH-B8      STELEFGSELIPISMADVQLQVSGGGSVQPGGSLRLSCAASGFTFSNYAMYWLRQAPGKG
VHH-E9      ------------------------------------------------------------
VHH-A10     ------------------------------------------------------------

VHH-E3      ------------------------------------------------------------
VHH-B8      IEWVSRIGPGGSHTEYADSVKGRFTISRDNAKNTLSLQMNSLKPEDTAVYYCAITQQGSG
VHH-E9      ------------------------------------------------------------
VHH-A10     ------------------------------------------------------------

VHH-E3      ---------------LEHHHHHH     (SEQ ID NO: 8)
VHH-B8      RGRGTQVTVSSAAASLEHHHHHH     (SEQ ID NO: 14)
VHH-E9      ---------------LEHHHHHH     (SEQ ID NO: 11)
VHH-A10     ---------------LEHHHHHH     (SEQ ID NO: 5)
                           ********
```

FIGURE 1

VARIABLE DOMAINS OF CAMELID HEAVY-CHAIN ANTIBODIES DIRECTED AGAINST GLIAL FIBRILLARY ACIDIC PROTEINS

The present invention relates to variable domains of camelid heavy-chain antibodies (VHH domains) directed against a glial fibrillary acidic protein (GFAP), and their use for delivering therapeutic or diagnostic compounds across the mammal blood-brain barrier and cell membranes.

Glial fibrillary acidic protein (GFAP) is a protein expressed in astrocytes of the central nervous system (CNS), the enteric glia, and in myelin-forming Schwann cells of the peripheral nervous system. GFAP, along with vimentin, is involved in the formation of type III intermediate filaments, which are important components of the cytoskeleton. GFAP is also involved in cell structure and movement (GFAP plays a role in mitosis), cell communication and the functioning of the blood brain barrier. A cDNA clone encoding a hGFAP has been disclosed by REEVES et al. (Proc Natl Acad Sci USA., 1989, 86:5178-82).

GFAP is regarded as one of the major immunocytochemical markers of the astrocytes, and also as a crucial marker of gliosis (i.e., the proliferation of astrocytes) in tumors of the central nervous system as well as degenerative or traumatic conditions of the brain tissues. The study of the structural organization and distribution of GFAP-positive astrocytes in different parts of the CNS, especially in the white matter, can also be relevant with respect to traumatic conditions.

Several brain disorders are associated with improper GFAP regulation. By way of example, glial scarring, in which the scar is formed by astrocytes interacting with fibrous tissue, is caused by up-regulation of GFAP. Another condition directly related to GFAP is Alexander disease. It has been showed that mutations in the coding region of the GFAP gene are associated with the presence of this disease (BRENNER et al., 2001, Nat Genet., 27:117-20).

Thus, there is a substantial interest in the development of adequate diagnostic agents to detect brain tumors or degenerative foci for instance, as well as therapeutic agents capable of treating disorders mediated by glial fibrillary acidic proteins (GFAPs).

Antibodies represent potential neuro-diagnostic imaging agents for brain disease as well as potential therapeutic agents. However, antibodies face several challenges: like other large plasma proteins such as albumin, they do not readily traverse cell membranes and are generally confined to the plasma compartment of the blood circulation. In case of an intracellular antigen, their stability and therefore their binding capacities is affected by the reducing conditions of the intracellular environment.

Over the past decade, there has been growing interest in the manufacturing and use of antibodies raised against intracellular targets. This is usually achieved through recombinant expression of a single chain variable domain (scFv) antibody within the cell. This type of antibody is commonly referred to as intrabody>>. The drawback of this method is the poor stability of the neo-synthesized intrabodies in their intracellular environment. The detrimental reducing conditions of the cytoplasm prevent the formation of intradomain disulfide bonds which in turn affects protein conformational folding. As a result, intrabodies can be non-fonctional, and show poor expression levels, low solubility, and a reduced half-life within the cell.

HAMERS-CASTERMAN (Nature, 1993, 363:446-8) have demonstrated that, in camelidae (camels, dromedaries, llamas and alpacas), about 50% of immunoglobulins are antibodies devoid of light chain. These heavy-chain antibodies interact with the antigen by the virtue of only one single variable domain, referred to as VHH(s), VHH domain(s) or VHH antibody(ies). Despite the absence of light chain, these homodimeric antibodies exhibit a broad antigen-binding repertoire by enlarging their hypervariable regions. Recombinant VHH domains (VHHs) are inherently thermostable (antigen binding of VHH being demonstrated at 90° C.) and exhibit the antigen-binding capacity of the camelid original heavy-chain antibody (NGUYEN et al., 2001, Adv. Immunol., 79, 261-96; MUYLDERMANS et al., 2001, Trends in Biochemical Sciences, 26:230-235). VHHs have also been shown to be extremely plastic in that, when they do eventually undergo denaturation, they are often capable of quantitative refolding. Small size (14-17 Kda) and increased plasticity appear to provide VHHs with unique potentialities: for instance, their diffusion into tissues is facilitated by their small size, and several VHHs are capable of inhibiting enzymatic activity by interacting with the active site cavity of enzymes such as alpha-amylase, carbonic anhydrase and hen egg lysozyme (DESMYTER et al., 1996, Nature Structural Biology, 3:803-11; DESMYTER et al., 2002, Journal of Biological Chemistry, 277:23645-23650; TRANSUE et al., 1998, Proteins, 32:515-22; LAUWEREYS et al., 1998, Embo J., 17:3512-20).

Within the framework of research that has led to the present invention, the Inventors have prepared camelid heavy-chain antibodies directed against GFAP and have analysed their binding properties both in vitro and in viva. Thus, one alpaca was immunized against hGFAP and three anti-GFAP VHHs were selected by ribosome display.

Surprisingly, the Inventors have demonstrated:
that the anti-GFAP VHHs strongly and specifically immunolabeled the GFAP protein in both human and mouse astrocytes on brain sections (this has been shown by standard immunocytochemical analysis, after fixation and permeabilisation of brain tissues). In this respect, these VHHs matched the properties of conventional anti-GFAP antibodies;
the ability of the anti-GFAP VHHs to diffuse into the brain, to enter into the cytoplasm of brain cells (particularly astrocytes), and to bind the GFAP in vivo (the VHHs strongly and specifically immunolabeled astrocytes present in the basal ganglion and around, after stereotaxic injections into the rostro-dorsal striatum of live mice);
the ability of the anti-GFAP VHHs to diffuse, reach and bind their intracerebral target after administration by intranasal instillation in vivo (as revealed by immunostaining of astrocytes present in the olfactory bulb and in the glia limitans of the cerebral forebrain); therefore, without requiring an injection of any sort, these VHHs can be easily delivered to the brain and penetrate into the neural and glial cells (particularly astrocytes). Thus, such VHHs can unexpectedly reach their intracellular target without any artificial treatment.

Therefore, these VHHs are interesting agents for brain imaging and delivering therapeutic compounds into the brain, particularly into the astrocytes.

Accordingly, the present invention provides a variable domain of a camelid heavy-chain antibody (VHH domain) directed against a glial fibrillary acidic protein (GFAP).

Particularly, the GFAP is from a warm-blooded animal, more particularly from a mammal, and especially from human origin. For instance, a human GFAP is available in the GENBANK database under the following accession numbers: gi:164694994 or gi:24430142.

A VHH domain refers usually to a variable domain of a camelid (camel, dromedary, llama, alpaca, . . . ) heavy-chain antibody (See NGUYEN et al., 2001, above-cited; MUYLDERMANS et al., 2001, above-cited).

According to the present invention, a VHH domain comprises an isolated, recombinant or synthetic VHH domain.

As used herein, the term "isolated" refers to a VHH domain which has been separated from a camelid heavy-chain antibody from which it derives.

As used herein, the term "recombinant" refers to the use of genetic engineering methods (cloning, amplification) to produce said VHH domain.

As used herein, the term "synthetic" refers to production by in vitro chemical or enzymatic synthesis.

Preferably, the VHH domain of the invention is from an alpaca (*Lama pacos*) heavy-chain antibody.

Preferably, the VHH domain of the invention consists of 100 to 130 amino acid residues.

The VHH domain can also be in the form of a dimer, preferably consisting of 245 to 265 amino acid residues.

In a preferred embodiment, the VHH domain of the invention has an isoelectric point of at least 8.5.

The term "isoelectric point" (pI) refers to the pH at which the VHH domain carries no net charge. Methods for determining the isoelectric point of a protein, particularly a peptide or protein, are well known to those of one skilled in the art. By way of example, many suitable computer programs for calculating the pI of a protein are generally known in the art, such as EMBOSS iep software, written by Alan Bleasby, available at HGMP-RC, Genome Campus, Hinxton, Cambridge CB10 1SB, UK.

In another preferred embodiment, the VHH domain of the invention comprises or consists of the consensus amino acid sequence SEQ ID NO: 1.

In a more preferred embodiment, the VHH domain of the invention comprises or consists of the amino acid sequence selected from the group consisting of SEQ ID NO: 3, SEQ ID NO: 6, SEQ ID NO: 9 and SEQ ID NO: 12.

The VHH domain of the invention can also comprise at least two amino acid sequences SEQ ID NO: 1, preferably two amino acid sequences SEQ ID NO: 6. For instance, the VHH domain of SEQ ID NO: 12 is an homodimer of the VHH domain of SEQ ID NO: 6.

A VHH domain of the invention is obtainable by the method comprising the steps of:
(a) immunizing a camelid, preferably a *Lama pacos*, with a GFAP as defined above,
(b) isolating peripheral lymphocytes of the immunized camelid, obtaining the total RNA and synthesizing the corresponding cDNAs (methods are known in the art; for instance see LAFAYE et al., 1995, Res Immune., 146:373-82; Erratum in: Res Immunol., 1996, 147:61),
(c) constructing a library of cDNA fragments encoding VHH domains,
(d) transcribing the VHH domain-encoding cDNAs obtained in step (c) to mRNA using PCR, converting the mRNA to ribosome display format, and selecting the VHH domain by ribosome display, and
(e) expressing the VHH domain in a vector (for instance, a suitable vector is pET22 (Novagen, Cat. No. 69744-3)) and, optionally purifying the expressed VHH domain.

In a preferred embodiment of said method, in step (a), the camelid is immunized at days 0, 21 and 35 with 250 μg of said GFAP. The bound camelid antibodies can be detected with polyclonal rabbit anti-camelid IgG (for instance, see MUYLDERMANS, Protein Eng., 1994, 7:1129-35) and horseradish peroxidase-labeled goat anti-rabbit antibodies.

In another preferred embodiment of said method, in step (c), said library can be constructed by amplifying by PCR the DNA fragments encoding the VHH domains, and ligating the PCR products obtained into a phage vector (an example of suitable phage vector is pHEN; HOOGENBOOM et al., J Mol Biol., 1992, 227:381-8).

In a particular embodiment of said step (c), the DNA fragments encoding VHH domains are amplified by PCR using the primers of sequences SEQ ID NO: 16 (named CH2FORTA4) and SEQ ID NO: 17 (named VHBACKA6), and the amplified product is subjected to a second round of PCR using either the primers of sequences SEQ ID NO: 18 (named VHBACKA4) and SEQ ID NO: 19 (named VHFOR36) or the primers VHBACKA4 and of sequence SEQ ID NO: 20 (named LH). Such a method is described in the International PCT Application No. WO 2004/044204.

In another preferred embodiment of said method, in step (d), said PCR is carried out using the primers of sequences SEQ ID NO: 21 (named VHH-SPEF) and SEQ ID NO: 22 (named VHH-SPER), and then the PCR product is amplified using a mixture of primers of sequences SEQ ID NO: 23 (named SDA-MRGS), SEQ ID NO: 24 (named T7C) and VHH-SPER. A peptide linker can also be added to ensure that the protein displayed on the ribosome is accessible to potential ligands. By way of example, a DNA encoding such a linker, that corresponds to a part of the *E. coli* protein TolA can be PCR amplified by using the primers of sequences SEQ ID NO: 25 (named VHH-link) and SEQ ID NO: 26 (named TolAkurz). The library of VHH domain-encoding cDNAs can be assembled with the TolA linker by PCR assembly using the primers TolAkurz and of sequence SEQ ID NO: 27 (named T7B).

Ribosome display technology enables in vitro selection of a protein together with the mRNA that encodes it. A DNA library coding for particular proteins, for instance VHH fragments, is transcribed in vitro. The mRNA is purified and used for in vitro translation. As the mRNA lacks a stop codon, the ribosome stalls at the end of the mRNA, giving rise to a ternary complex of mRNA, ribosome and functional protein (HANES and PLUCKTUM, 1997, Proc. Natl. Acad. Sci. USA, 94:4937-42). A library of these ternary complexes is tested against the potential ligand (in the case of antibodies, against the antigen). The binding of the ternary complex (ribosome, mRNA, protein) to the ligand allows the recovery of the encoding mRNA that is linked to it and that can be transcribed into cDNA by Reverse Transcriptase-PCR (RT-PCR). Cycles of selection and recovery can be iterated both to enrich rare ligand-binding molecules, and to select molecules with the best affinity.

Methods for ribosome display selections are known in the art; for instance, see MOURATOU et al., 2007, Proc Natl Acad Sci USA., 104:17983-8.

In another preferred embodiment of said step (d), the ribosome display selection is performed in three PCR rounds. Preferably, a first PCR is done using the primers VHH-SPEF and VHH-SPER, the PCR product obtained after the first PCR is reamplified in a second PCR using the primers T7C, SDA-MRGS and VHH-SPER, and the PCR product obtained after the second PCR is reamplified in a third PCR using the primers T7B and TolAkurz, and the third PCR product serves as template for a next round of ribosome display.

The Inventors have generated a library of cDNA fragments encoding VHH domains directed against a hGFAP protein (accession number gi:164694994 in the GENBANK database) using the method as described above (see also Example 1).

The present invention also provides a polypeptide comprising a VHH domain as defined above.

When the polypeptide of the present invention comprises at least two VHH domains as defined above, then said VHH domains can be identical or different and can be separated from one another by a spacer, preferably an amino acid spacer.

In order to allow the purification of a polypeptide of the present invention, said polypeptide can contain at its C-terminus an His-tag, such as the amino acid sequence LEHHHHHH (SEQ ID NO: 15).

Therefore, in an embodiment of said polypeptide, it further contains at the C-terminus of its amino acid sequence the amino acid sequence LEHHHHHH (SEQ ID NO: 15). By way of example, the polypeptides of amino acid sequences SEQ ID NO: 5 (named VHH-A10), SEQ ID NO: 8 (named VHH-E3), SEQ ID NO: 11 (named VHH-E9) and SEQ ID NO: 14 (named VHH-B8) consist of the VHH domains of sequences SEQ ID NO: 3, 6, 9 and 12 respectively to which the amino acid sequence LEHHHHHH has been fused.

In a preferred embodiment, the VHH domain or polypeptide of the invention binds to a GFAP as defined above with a binding affinity of at least $<10^{-6}$ M. Affinity (dissociation constant) measurements may be made using methods known to those skilled in the art, including the methods described in FRIGUET et al. (J. Immunol. Methods, 1985, 77:305-319).

VHH-A10, VHH-E3, VHH-E9 and VHH-B8 possess an affinity for the hGFAP (gi:164694994 in the GENBANK database) of $3.1 \times 10^{-9}$ M, between $10^{-7}$ and $10^{-6}$ M, $5.6 \times 10^{-9}$M and $5.2 \times 10^{-9}$M respectively (affinity measured according to the method described in FRIGUET et al. (above-cited)).

The present invention also provides isolated antibodies, preferably camelid heavy-chain antibodies, or fragments thereof, comprising a VHH domain of the invention, wherein said isolated antibodies or fragments thereof bind to a GFAP as defined above.

As used herein, the terms "antibody fragment" means a portion of a full-length (whole) antibody, e.g., only one heavy chain or the Fab region.

The present invention also provides isolated polynucleotides encoding a VHH domain, a polypeptide, or an antibody or fragment thereof of the present invention. Polynucleotides of the invention may be obtained by the well-known methods of recombinant DNA technology and/or of chemical DNA synthesis.

In a particular embodiment of said polynucleotide, it is a cDNA derived from a gene encoding a VHH domain with no hinge or with a long hinge.

Nucleotide sequences encoding VHH-A10, -E3, -E9 and -B8 are annexed in the herewith attached sequence listing as SEQ ID NO: 4, 7, 10 and 13.

The present invention also provides recombinant expression cassettes comprising a polynucleotide of the invention under the control of a transcriptional promoter allowing the regulation of the transcription of said polynucleotide in a host cell. Said polynucleotide can also be linked to appropriate control sequences allowing the regulation of its translation in a host cell.

The present invention also provides recombinant vectors comprising a polynucleotide or an expression cassette of the invention.

The present invention also provides a host cell containing a recombinant expression cassette or a recombinant vector of the invention. The host cell is either a prokaryotic or eukaryotic host cell.

A prokaryotic host cell expressing VHH-A10 has been deposited at the Collection Nationale de Cultures de Microorganismes (CNCM), 28 rue du Dr Roux, 75724 Paris Cedex 15, France, under the number I-3923.

A prokaryotic host cell expressing VHH-B3 has been deposited at the CNCM, under the number I-3924.

A prokaryotic host cell expressing VHH-E3 has been deposited at the CNCM, under the number I-3925.

A prokaryotic host cell expressing VHH-E9 has been deposited at the CNCM, under the number I-3926.

The present invention also provides a therapeutic or diagnostic agent comprising a VHH domain, polypeptide or antibody of the present invention, linked, directly or indirectly, covalently or non-covalently to a substance of interest.

The substance of interest according to the present invention may or may not permeate the mammal or human blood-brain barrier or cell (e.g., astrocyte) membranes. If the substance of interest permeates said blood-brain barrier or cell (e.g., astrocyte) membranes, then the use of a VHH domain, polypeptide or antibody of the present invention can allow enhancing the delivery of said substance of interest across the blood-brain barrier or into the cells (in particular astrocytes).

In an embodiment of said therapeutic or diagnostic agent, said substance of interest is a therapeutic or diagnostic compound selected from the group consisting of a peptide, an enzyme, a nucleic acid, a virus, a fluorophore, a heavy metal, a chemical entity and a radioisotope.

In another embodiment of said therapeutic or diagnostic agent, the substance of interest is a liposome or a polymeric entity comprising a therapeutic or a diagnostic compound as defined above.

In a preferred embodiment of said diagnostic agent, said diagnostic compound is selected from the group consisting of:

enzymes such as horseradish peroxidase, alkaline phosphatase, glucose-6-phosphatase or beta-galactosidase;

fluorophores such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers);

heavy metal chelates such as europium, lanthanum or yttrium;

radioisotopes such as [$^{18}$F]fluorodeoxyglucose, $^{11}$C-, $^{125}$I-, $^{131}$I-, $^{3}$H-, $^{14}$C-, $^{35}$S, or $^{99}$Tc-labelled compounds.

In another preferred embodiment of said therapeutic agent, said therapeutic compound is selected from the group consisting of an anticancer compound, an analgesic compound, an anti-inflammatory compound, an antidepressant compound, an anticonvulsant compound or an anti-neurodegenerative compound.

The substance of interest as defined above can be directly and covalently or non-covalently linked to the VHH domain, polypeptide or antibody of the present invention either to one of the terminal ends (N or C terminus) of said VHH domain, polypeptide or antibody, or to the side chain of one of the amino acids of said VHH domain, polypeptide or antibody. The substance of interest can also be indirectly and covalently or non-covalently linked to said VHH domain, polypeptide or antibody by a connecting arm (i.e., a cross-linking reagent) either to one of the terminal ends of said VHH domain, polypeptide or antibody, or to a side chain of one of the amino acids of said VHH domain, polypeptide or antibody. Linking methods of a substance of interest to a peptide, in particular an antibody, are known in the art (e.g., See TERNYNCK and AVRAMEAS, 1987, "Techniques immunoenzymatiques" Ed. INSERM, Paris).

Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

Alternatively, if the substance of interest is a peptide, the VHH domain, polypeptide or antibody of the present invention and said substance of interest can be produced by genetic engineering as a fusion polypeptide that includes the VHH domain, polypeptide or antibody of the invention and the suitable peptide. This fusion polypeptide can conveniently be expressed in known suitable host cells.

The VHH domain, the polypeptide, the antibody, the therapeutic or diagnostic agent, or the polynucleotide of the present invention can be administered to a subject (a mammal or a human) by injection, such as intravenous, intraperitoneal, intramuscular or subcutaneous injection, or by intranasal instillation.

Advantageously, when the VHH domain, the polypeptide or antibody of the present invention is administered to a subject by intranasal instillation, then it can reach and penetrate into the astrocytes.

A diagnostic agent of the present invention can be used in brain imaging, in diagnosing or monitoring brain disorders such as brain cancers, gliosis, astrocytoma, Alexander disease, degenerative foci, pain, mental disorders (for instance, depression) or neurodegenerative disorders (for instance: Alzheimer's disease).

The present invention also provides a kit for brain imaging, or for diagnosing or monitoring a brain disorder as defined above, comprising at least a VHH domain, a polypeptide, an antibody, a diagnostic agent or a polynucleotide of the present invention.

The present invention also provides a method of diagnostic of a disorder mediated by glial fibrillary acidic proteins (GFAPs), such as Alexander disease, gliosis, astrocytoma, in a subject comprising the steps of:
  a) contacting in vitro or ex vivo an appropriate biological sample with a polypeptide or a diagnostic agent of the present invention,
  b) determining the amount of GFAPs in said biological sample, and
  c) comparing the amount determined in step (b) with a standard, a difference in amount constituting a marker of the presence of said disorder.

The present invention also provides a pharmaceutical composition comprising a therapeutic agent as defined above and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

The present invention also provides a VHH domain, a polypeptide, an antibody, a therapeutic agent, a pharmaceutical composition or a polynucleotide of the present invention for use in the treatment of a disorder mediated by glial fibrillary acidic proteins (GFAPs), such as Alexander disease, gliosis or astrocytoma, or for use in the treatment of brain cancers, astrocytoma, pain, mental disorders or neurodegenerative disorders.

As used herein, the term "treatment" includes the administration of the VHH domain, polypeptide, antibody, therapeutic agent or pharmaceutical composition as defined above to a patient who has a disorder, a symptom of disorder or a predisposition toward a disorder, with the purpose to cure, heal, alleviate, relieve, alter, remedy, ameliorate, improve or affect the disorder, the symptoms of the disorder, or the predisposition toward disorder.

In another aspect, the present invention relates to the use of a VHH domain, polypeptide or antibody of the invention, for the preparation of a peptide vector for delivering a substance of interest as defined above across a mammal blood-brain barrier or a cell membrane, preferably a human blood-brain barrier or cell membrane.

Particularly, a VHH domain, a polypeptide or an antibody of the invention can be used for the preparation of a peptide vector for delivering a substance of interest as defined above across the mammal astrocyte membrane, preferably the human astrocyte membrane, or for delivering a substance of interest as defined above into mammal astrocytes, preferably human astrocytes.

The Inventors have found unexpectedly that a VHH domain of the invention which has naturally an isoelectric point equal to 9.15, does not have a modified affinity for its antigen and can act as a transbody and intrabody in vitro as well as in vivo (See Example 4).

Therefore, in another aspect, the present invention relates to the use of a variable domain of a camelid heavy-chain antibody (VHH domain) directed against an intracellular target and having an isoelectric point of at least 8.5, preferably of at least 9, and more preferably between 9 and 10, or of a polypeptide or antibody comprising said VHH domain, for targeting said intracellular target or for the preparation of a peptide vector for delivering a substance of interest, as defined above, into a mammal cell, preferably a human cell, comprising said intracellular target.

As used herein the term "intracellular target" refers to any antigen (or moiety) present inside a cell, preferably a brain cell, such as a neuron or a glial cell, and capable of directing said VHH domain, or polypeptide or antibody comprising said VHH domain, inside said cell by virtue of its ability to bind or interact with said VHH domain.

As used herein the term "targeting" refers to the ability of a VHH domain, polypeptide or antibody, as defined above, to enter a cell, preferably a brain cell, such as a neuron or a glial cell, and bind said intracellular target (antigen).

In a preferred embodiment of this aspect, said VHH domain is hyperstable.

As used herein, the term "hyperstable" means that a VHH domain can recover its active activity (or function) after denaturation by heat (then said VHH domain is thermostable) and/or after reduction of its disulfide bridge(s).

The thermostability of a VHH domain can be determined as follows:
a) suspending a VHH domain (named "native VHH domain") in PBS/NaCl 300 mM,
b) heating for 15 minutes at 75° C.,
c) cooling down at 4° C. for 20 minutes,
d) determining the binding affinity of the refolded VHH domain obtained at step c), and if the stability of the refolded VHH domain is reduced at most twice compared to the native VHH domain then said VHH domain is thermostable.

The reduction of the disulfide bridge(s) of a VHH domain can be carried out as described in Example 4. According to the present invention, a VHH domain is hyperstable if the binding affinity of a VHH domain, of which the disulfide forming cysteine residues have been replaced with serine residues, is reduced at most twice compared to the native VHH domain.

The binding affinity of a VHH domain (VHH antibody) can be determined by any method known from one skilled in the art, for instance by the ELISA technique described in Example 1 below.

In another preferred embodiment of this aspect, said human cell is an astrocyte, and optionally said intracellular target is a GFAP.

The present invention also provides a method for screening compounds capable of modulating the quantity of GFAP proteins in a cell, preferably in an astrocyte, comprising the steps of:
a) contacting in vitro, ex vivo or in vivo said cell with a test compound,
b) detecting and determining the amount of GFAP proteins in said cell with a diagnostic agent of the present invention,
c) comparing the amount determined in step b) with the amount of GFAP proteins is said cell in absence of said test compound, wherein a difference in amount is indicative that said test compound is capable of modulating the quantity of GFAP proteins in said cell.

As used herein, the term "modulating the quantity of GFAP proteins" means decreasing or increasing the quantity of GFAP proteins or inhibiting the production of GFAP proteins.

In addition to the preceding features, the invention further comprises other features which will emerge from the following description, which refers to examples illustrating the present invention, as well as to the appended figures.

FIG. 1 shows the protein alignment of the anti-GFAP VHH domains VHH-E3 (SEQ ID NO: 8), VHH-B8 (SEQ ID NO: 14), VHH-E9 (SEQ ID NO: 11) and VHH-A10 SEQ ID NO: 5) carried out with the CLUSTAL W2 program (LARKIN et al., Bioinformatics, 2007, 23:2947-2948). VHH-B8 is duplicated and the corresponding monomer is identical to VHH-E3. (:) denotes similar substitutions and (.) denotes conserved substitutions.

Figure 5:
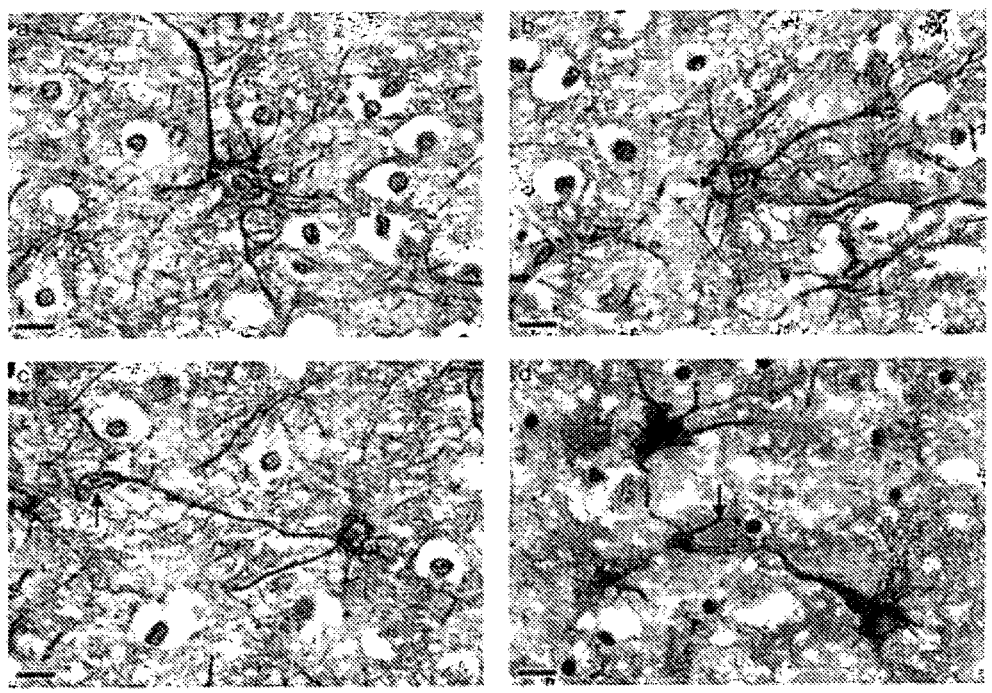

FIG. 5 shows the immunolabelling of the GFAP protein in astrocytes of brain sections from a Human being. Counterstain: Harris haematoxylin. White matter of the hippocampal formation. a and b: the immunolabeling is close to the cell membrane (arrowhead) and does not fill the cell body. In c and d, an astrocytic foot reaches a capillary (arrow). Scale Bar: 10 μm.

Figure 6:
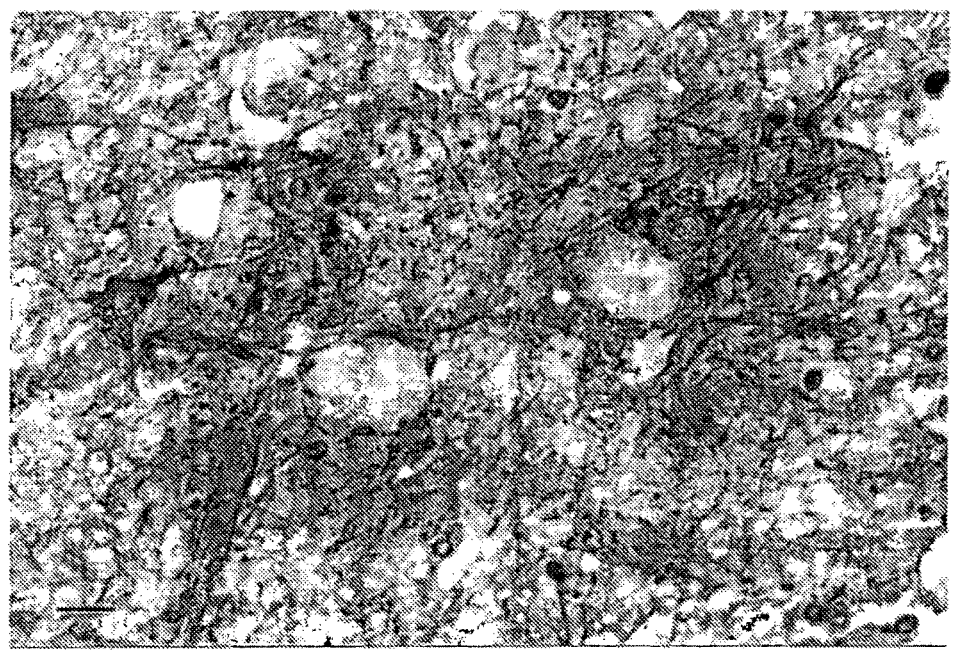

FIG. 6 shows the immunolabelling of the GFAP protein in astrocytes of brain sections from human patient with Alzheimer disease (AD). Sample from hippocampus. The processes of immunolabeled astrocytes surround two amyloid plaques. Scale Bar: 10 μm.

Figure 7:
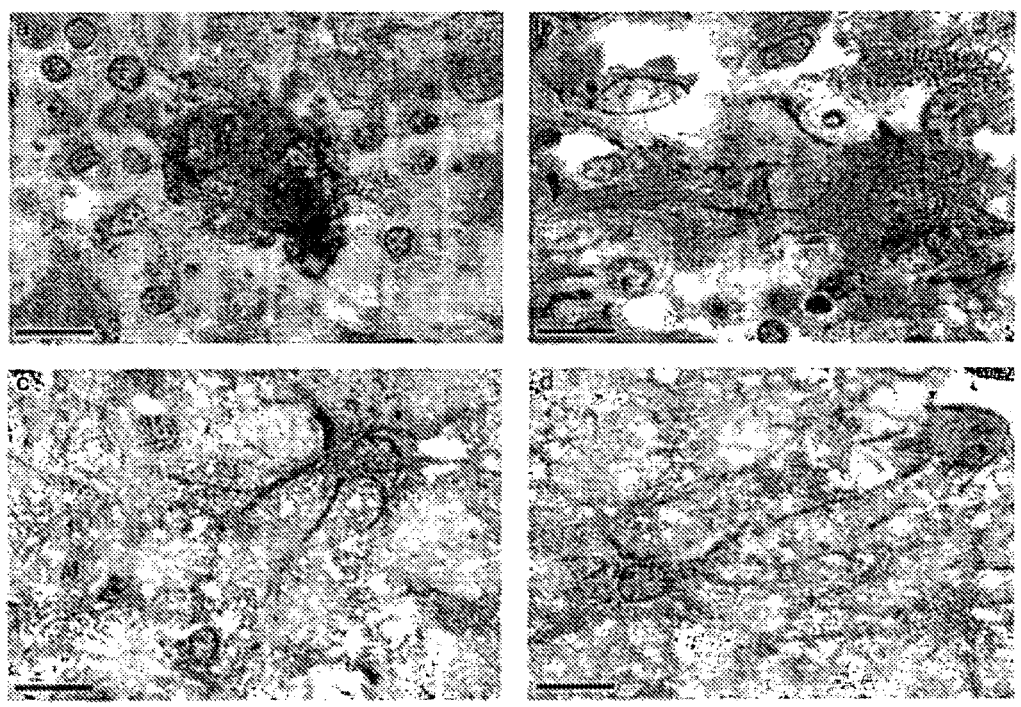

FIG. 7 shows the immunolabelling of GFAP in astrocytes of brain sections from astrocytoma. a and b: abnormal astrocytes in the tumor. c and d: reactive astrocyte at the periphery of the tumor. Scale Bar: 10 μm.

Figure 8:
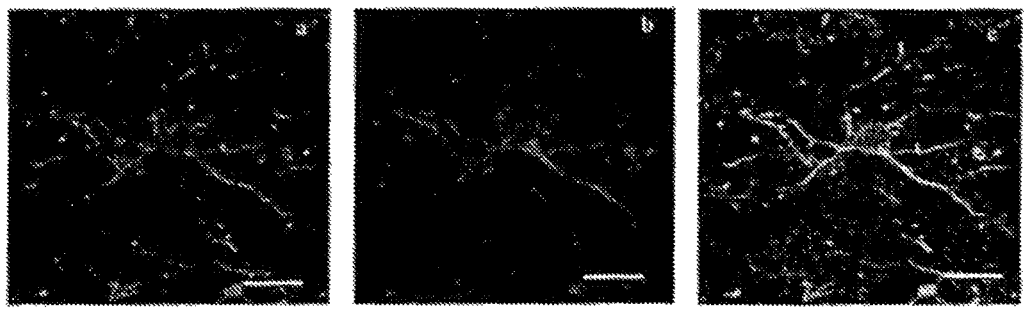

FIG. 8 shows double immunolabeling in a sample from an Alzheimer Patient by Confocal Microscopy. a: Alpaga anti-GFAP revealed by rabbit anti-His Tag antibodies and goat anti-Rabbit antibodies coupled with CY2. b: anti-GFAP mouse mAb revealed by goat anti-mouse antibodies coupled with CY3. c: Merged picture. Colocalization (yellow) was observed in glial fibers: in the cell body around nucleus, in processes and in perivascular astrocytic feet. Scale Bar: 10 μm.

Figure 9:
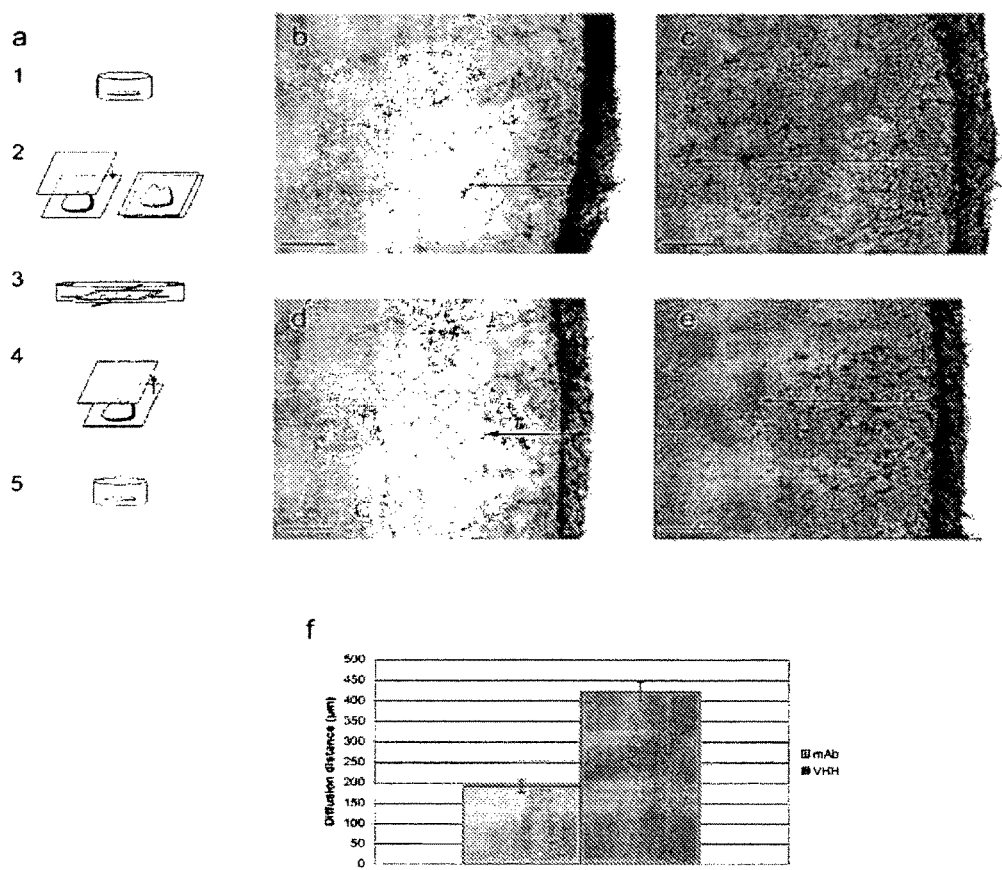

FIG. 9 shows the comparison of the diffusion of VHH-A10 and mAb. a: Diagram showing the various steps used to limit the diffusion of the $V_H H$ and mouse mAb to the edges by applying coverslips on the two sides. The secondary antibody was applied and the detection was performed on free floating sections. (1) Pretreatment, (2) The section was placed between 2 coverslips, (3) The section between the 2 coverslips was left in contact with the solution containing the primary antibody for 8 hours, (4) The section was taken off the coverslips, (5) The secondary antibody was applied and was detected on the free floating sections.

Figure 10:
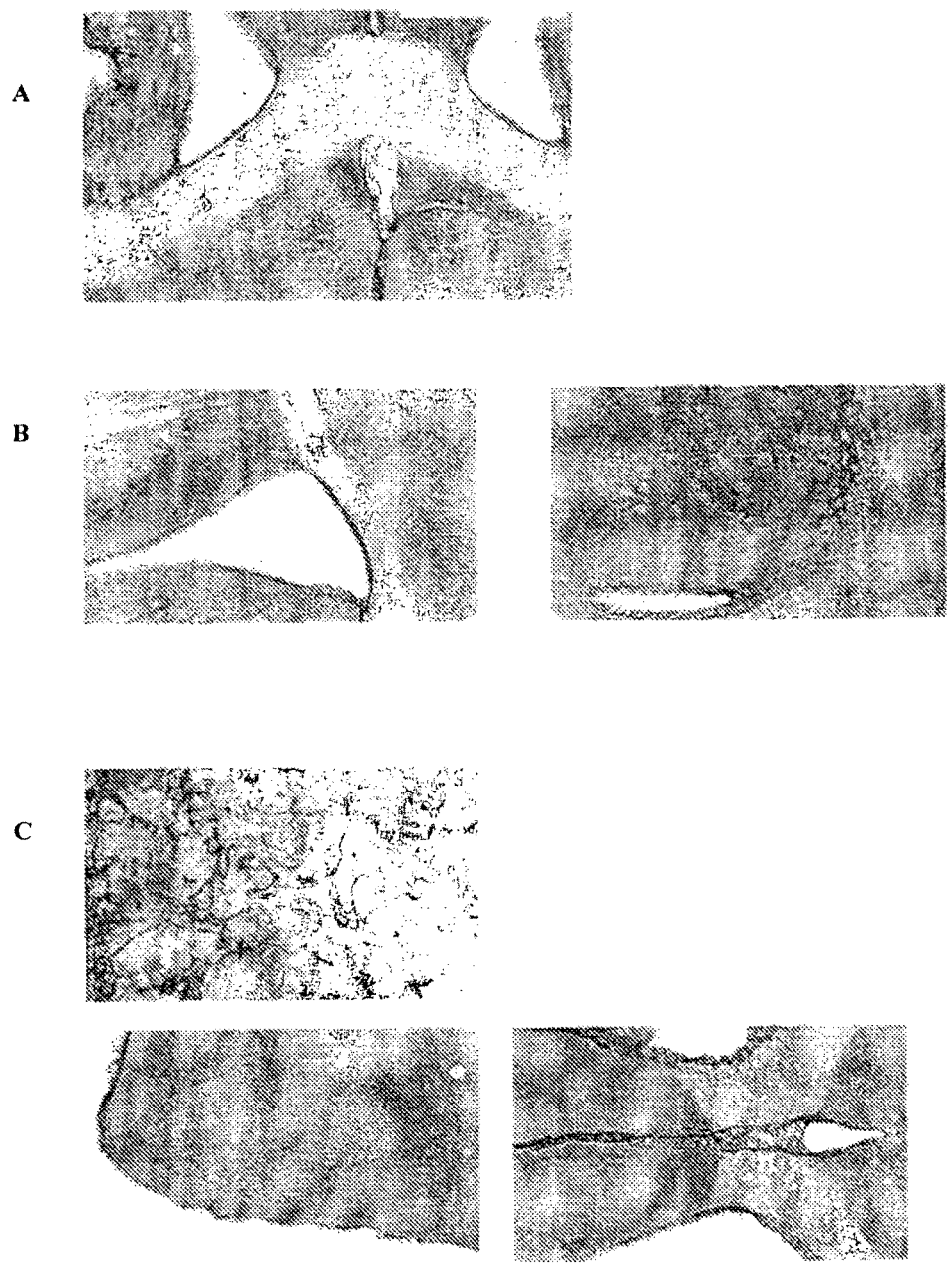

FIG. 10 shows the immunolabelling of the GFAP protein in astrocytes of murine brain sections. The VHH-A10 was stereotaxically injected into the live rostro-dorsal striatum prior to aldehydic fixation and immunostaining procedure. The brains were perfused 5 (A), 7 (B), or 14 (C) hours after the injection of the VHH.

Figure 11:

FIG. 11 shows the immunolabelling of the GFAP protein in astrocytes of murine brain sections. The VHH-A10 was delivered to the live brain via nasal instillations prior to aldehydic fixation and immunostaining procedure. Pictures correspond to two regions of the olfactive bulb.

Figure 12:
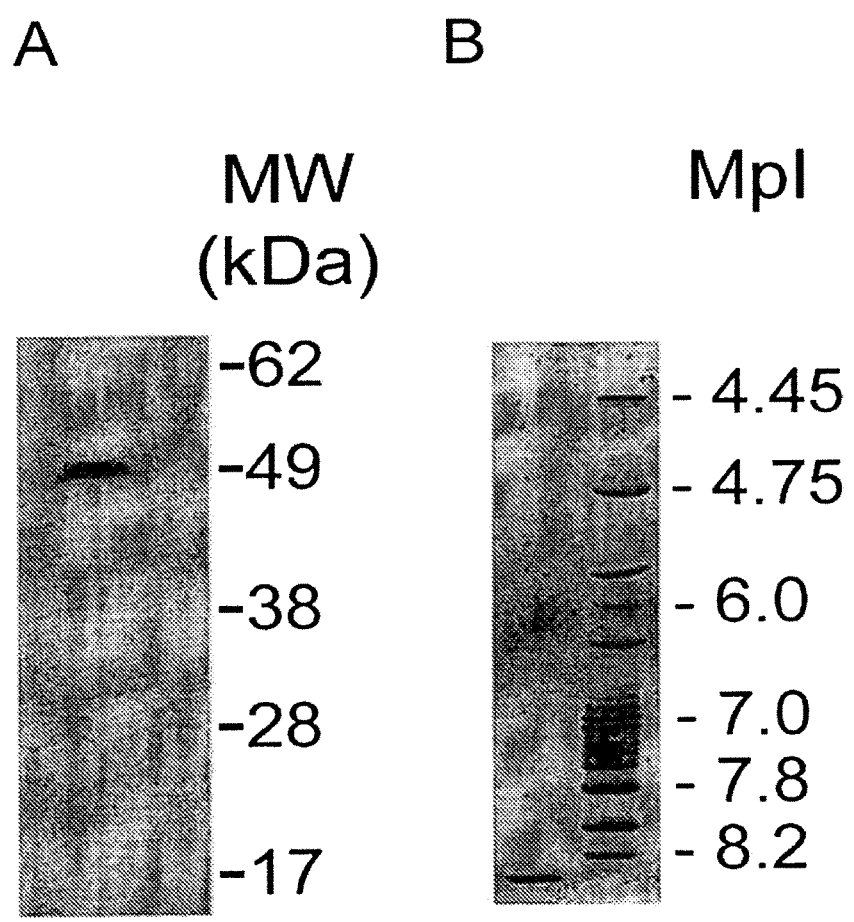

FIG. 12 shows the characterization of anti-GFAP VHH-E9. A: Western blot. Murine brain extracts were electrophoresed, immunoblotted and incubated with VHH-E9. MW: molecular weight marker proteins. B: Isoelectric focusing on PhastGel IEF 3-9. MpI: isoelectric point marker.

Figure 13:
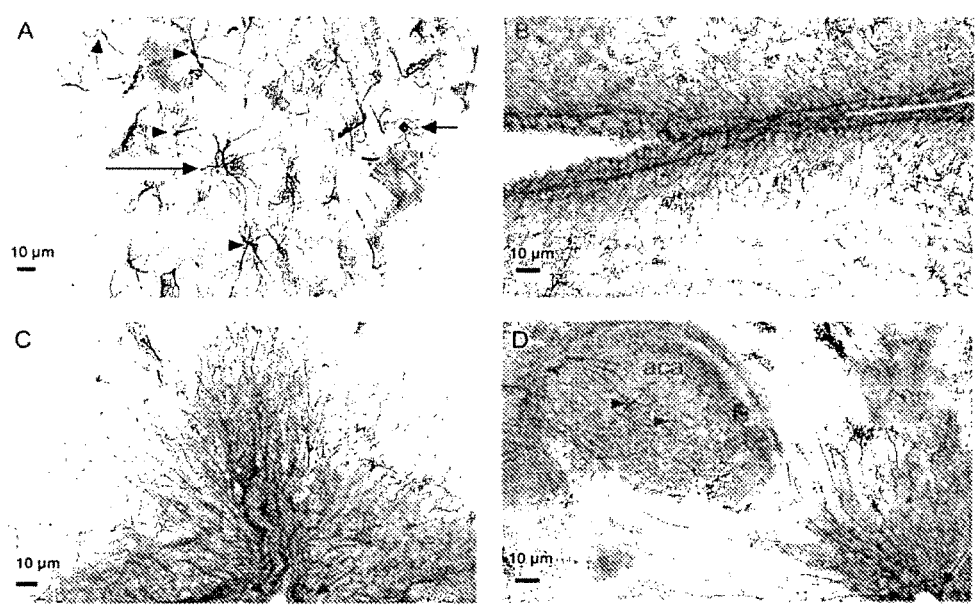

FIG. 13 shows the VHH-E9 immunolabeling of GFAP in the cytoplasm of astrocytes in mouse brain sections. A: Immunolabeled astrocytes in the white matter between striatum and primary motor cortex, close to the corpus callosum. It was mainly identify thin fibrous astrocytes (arrowheads) and some large protoplasmic astrocytes (arrow). B: immunolabeled astrocytic radially oriented processes beaming from the pial surface glia limitans (arrows) at level of the dorsal third ventricle. C: immunolabeled astrocytic radially organized glial processes beaming from the pial surface glia limitans (arrows) located at the base of the forebrain. These processes spread out through the antero-ventral periventricular and medial preoptic nuclei. D: immunolabeled astrocytes processes located in the cylindrical white matter of the anterior commissure, anterior part (aca; arrowheads). In the vicinity of aca are located also radially oriented immunolabeled GFAP fibers. These glial processes are beaming from a folded portion of the pial surface located in the bottom of the lateral ventricle (arrows).

Figure 14:
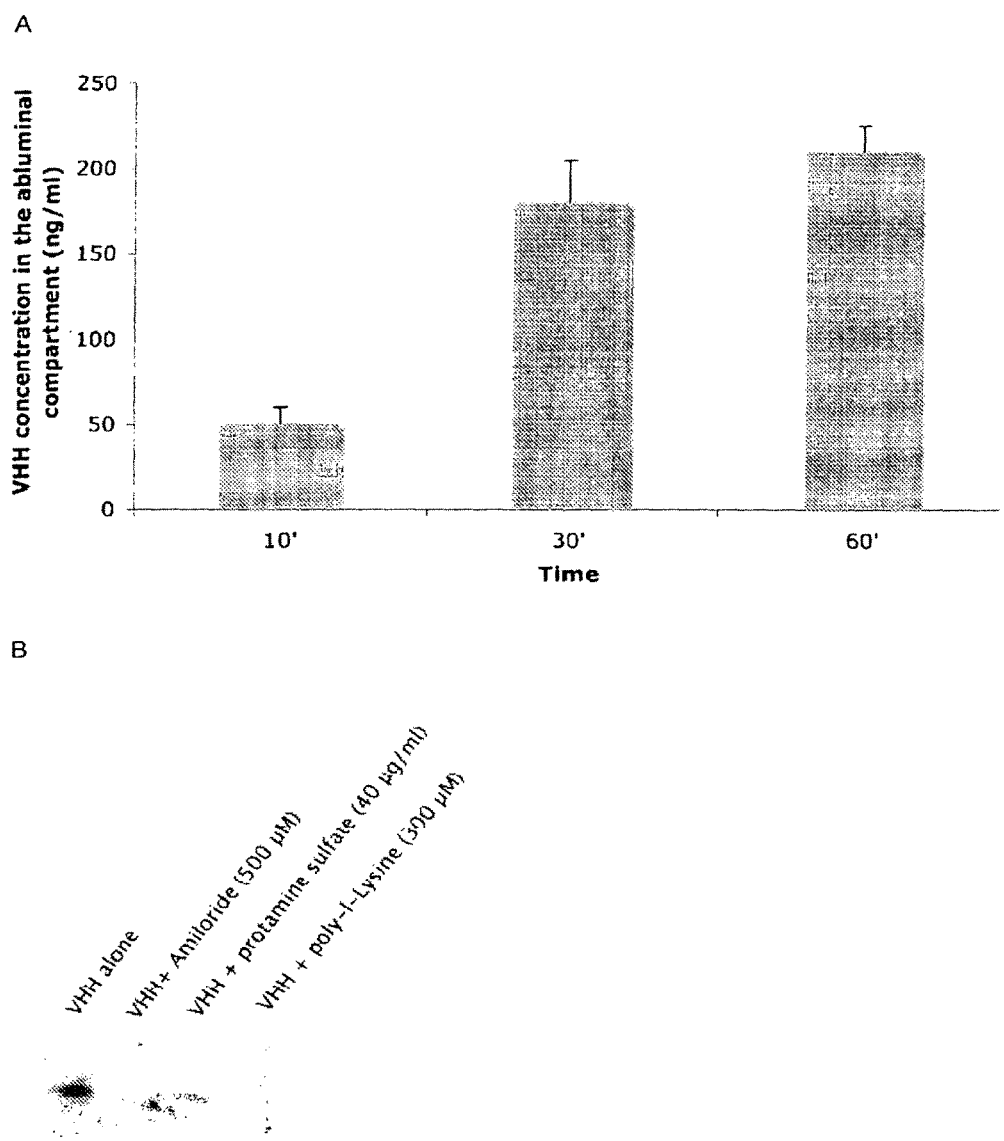

FIG. 14 shows the VHH-E9 transmigration across in vitro blood-brain barrier (BBB). A: Transport studies were initiated by adding 10-20 μg/ml VHH to the apical compartment (upper chamber) and the amount of VHH was determined in the lower chamber after 10 min, 30 min and 60 min. B: Effects of pharmacological inhibitors of adsorptive-mediated endocytosis (AME) and macropinocytosis on transmigration of VHH across in vitro BBB model. hCMEC/D3 were pretreated for 30 min with either AME inhibitors, protamine sulfate (40 μg/ml), and poly-L-lysine (300 μM), or micropinocytosis inhibitor, amiloride (500 μM). VHH transport was then measured over 30 min.

Figure 15:
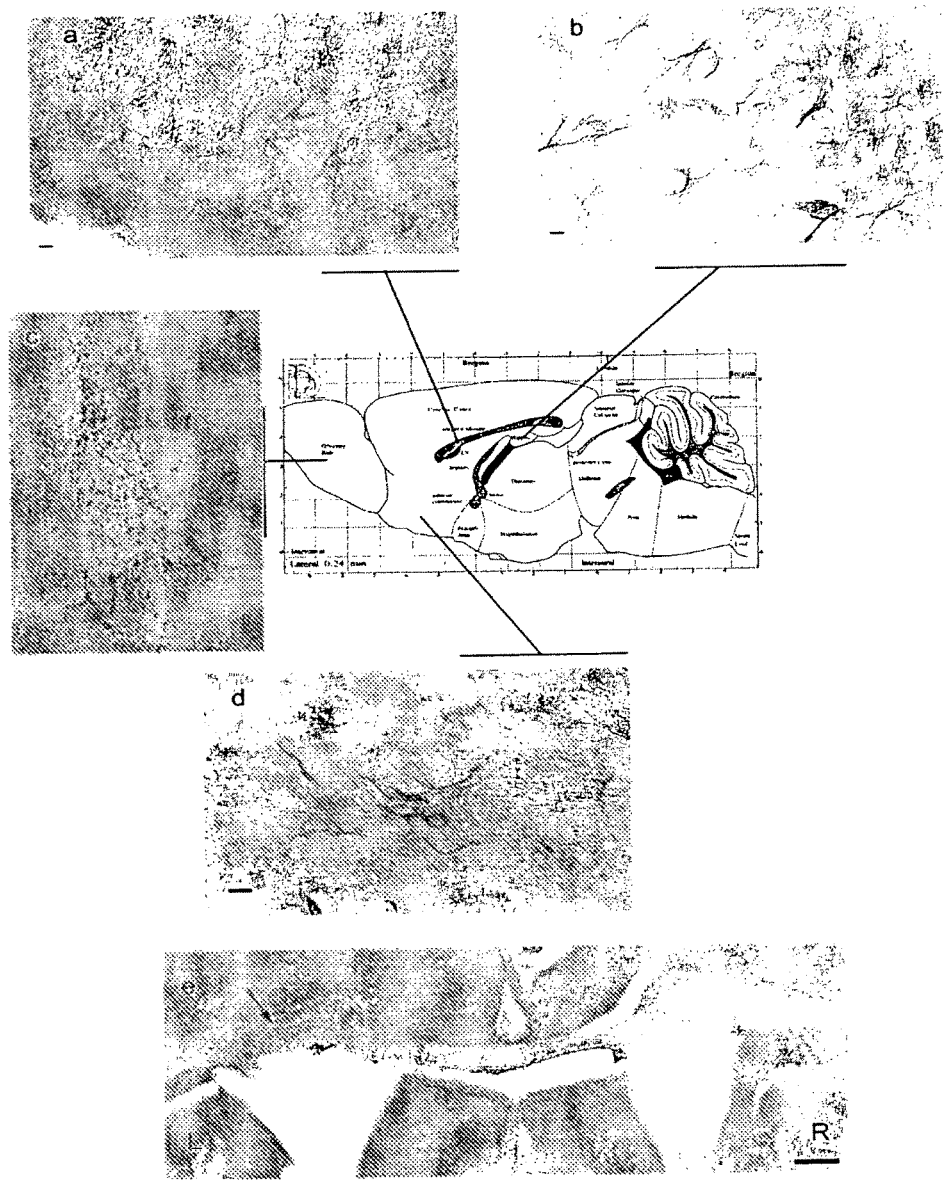

FIG. 15 shows the VHH-E9 transmigration across blood-brain barrier (BBB) in vivo. 4 mg of VHH were perfused in the left carotide artery of C57BL/6 mice for 60 min. Mice were euthanized 1 hour later. Immunolabeled astrocytes in a: the corpus callosum, b: hippocampus, c: olfactory bulb, d: gray matter (scale bar: 10 μm), e: coronal section of the rostral corpus callosum. More astrocytes are labelled in left (L) genu of the corpus callosum (arrow), ipsilateral to the injected carotide artery, as compared to the right side (R) (scale bar: 100 μm).

Figure 16:
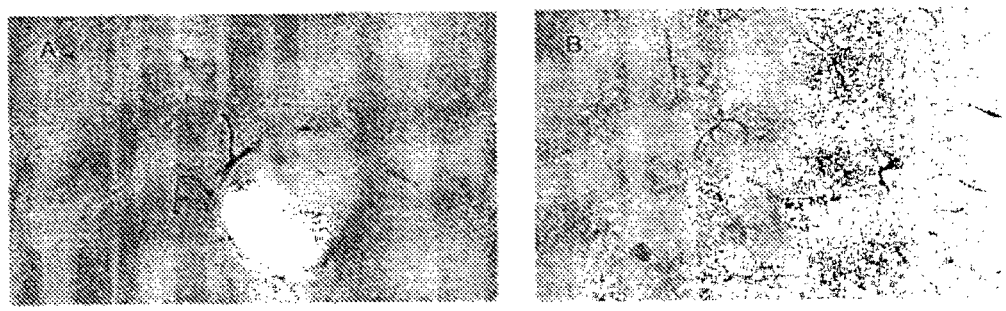

FIG. 16 shows the VHH-E9 immunolabelling of GFAP in mouse brain sections after injection of 30% mannitol. a: Glial astrocytic foot process apposed to a blood vessel, b: VHH immunolabelling of astrocytes in the white matter.

Figure 17:
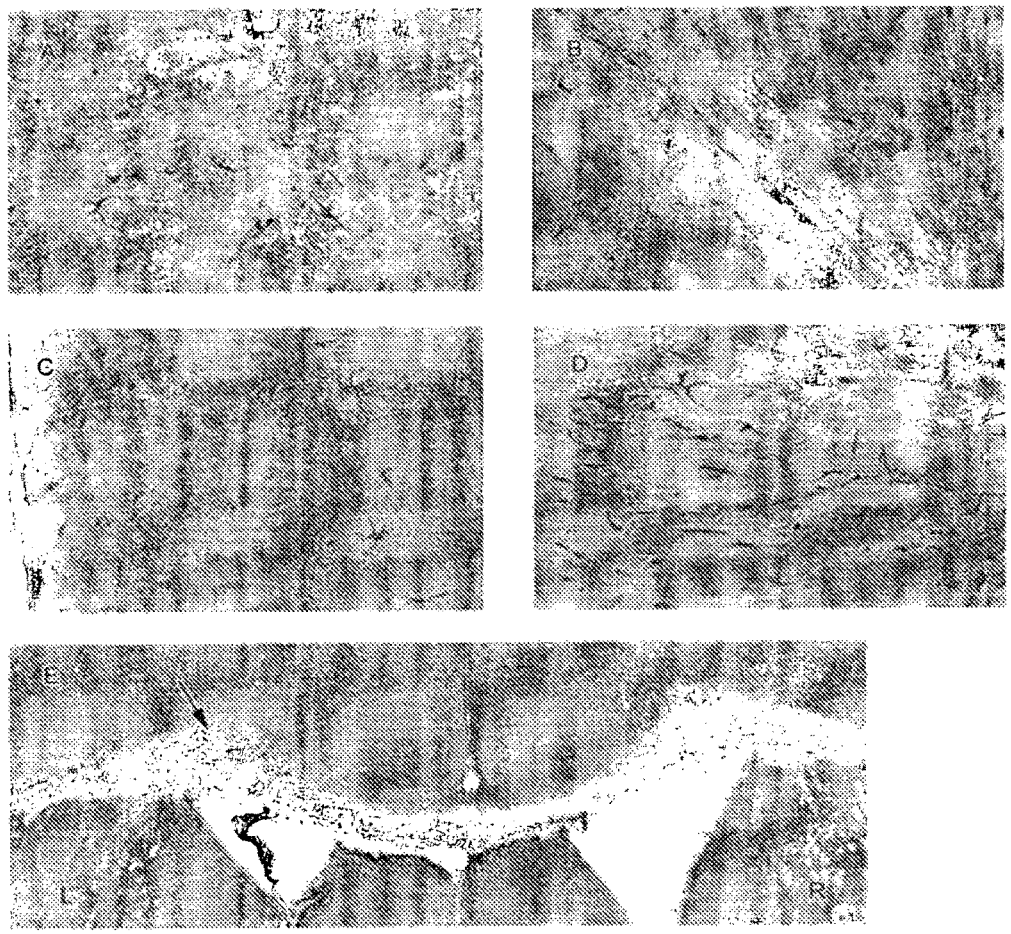

FIG. 17 shows the VHH-E9 labelling of GFAP in the cytoplasm of mice brain sections after infection with *Pl. berghei* parasite. C57BL/6 mice were inoculated i.p. with $10^6$ infected erythrocytes of *Pl. berghei* per mouse. At day 5, 400 μg of VHH were perfused in the left carotide for 60 min. Mice were killed 1 hour later. A: olfactif bulb, B: White matter, C: hippocampus, D: Caudal region, E: coronal section of the white matter. Astrocytes are labelled in the corpus callosum (L is the left hemisphere, corresponding to the side of the injected carotid; R is the right hemisphere).

The following examples illustrate the invention but in no way limit it.

EXAMPLE 1: PRODUCTION OF ANTI-GFAP-VHHS

1) Materials and Methods

Materials

GFAP (gi:164694994 in the GENBANK database) from normal human brain was purchased from United States Biological, Inc. The anti-GFAP rabbit polyclonal antibody (GF 5) was obtained from Santa Cruz Biotechnology, Ca, USA.

Primers:

-CH2FORTA4 (SEQ ID NO: 16):
5'-CGCCATCAAGGTACCAGTTGA-3'

-VHBACKA6 (SEQ ID NO: 17):
5'-GATGTGCAGCTGCAGGCGTCTGGRGGAGG-3'

-VHBACKA4 (SEQ ID NO: 18):
5'-CATGCCATGACTCGCGGCCCAGCCGGCCATGGCCGAKGTSCAGCT-3'

-VHFOR36 (SEQ ID NO: 19):
5'-GGACTAGTTGCGGCCGCTGAGGAGACGGTGACCTG-3'

-LH (SEQ ID NO: 20):
5'-GGACTAGTTGCGGCCGCTGGTTGTGGTTTTGGTGTCTTGGG-3'

VHH-SPEF (SEQ ID NO: 21):
5'GGAGATATATATCCATGAGAGGATCGCATCACCATCACCATCACGGATCCGCCGAKGTSCAGCTG-3'

-VHH-SPER (SEQ ID NO: 22):
5'-CCATATAAAGCTTTGAGGAGACGGTGACCTG-3'

-SDA-MRGS (SEQ ID NO: 23):
5'AGACCACAACGGTTTCCCTCTAGAAATAATTTTGTTTAACTTTAAGAAGGAGATATATCCATGAGAGGATCG-3'

T7C primer (SEQ ID NO: 24):
5'ATACGAAATTAATACGACTCACTATAGGGAGACCACAACGGTTTCCCTC-3'

-VHH-link (SEQ ID NO: 25):
5'-CAGGTCACCGTCTCCTCAAAGCTTTATATGGCCTCGGGGGCC-3'

-TolAkurz (SEQ ID NO: 26):
5'-CCGCACACCAGTAAGGTGTGCGGTTTCAGTTGCCGCTTTCTTTCT-3'

-T7B (SEQ ID NO: 27):
5'-ATACGAAATTAATACGACTCACTATAGGGAGACCACAACGG-3'

Antigen Preparation and Induction of a Humoral Immune Response in Alpaca

250 μl of GFAP (1 mg/ml) was mixed with 250 μl of Freund complete adjuvant for the first immunization, and with 250 μl of Freund incomplete adjuvant for the following immunizations.

One young adult male alpaca (*Lama pacos*) was immunized at days 0, 21 and 35 with 250 μg of the immunogen. The alpaca was bled and the immune response was monitored by titration of serum samples by ELISA on GFAP (1 μg/ml in PBS) immobilized on MaxiSorp™ plates (Nunc, Denmark), after dilution of the serum in PBS-Tween 0.1% containing 0.5% gelatin. The bound alpaca antibodies were detected with polyclonal rabbit anti-alpaca IgG (obtained by immunizing rabbits with alpaca immunoglobulins isolated with protein A and protein G columns [MUYLDERMANS et al., 1994, above-cited) and horseradish peroxidase-labeled goat anti-rabbit antibodies.

Library Construction

The blood of the immunized animal was collected and the peripheral blood lymphocytes were isolated by centrifugation on a Ficoll (Pharmacia) discontinuous gradient and stored at ~80° C. until further use. Total RNA and cDNA was obtained as previously described by LAFAYE et al., 1995 (Res Immune., 146:373-82; Erratum in: Res Immunol., 1996, 147:61). DNA fragments encoding VHH domains were amplified by PCR using CH2FORTA4 and VHBACKA6 primers (described in International Application No. WO 2004/044204; LAFAYE, above-cited), which respectively anneal to the 3' and 5' flanking region of VH genes (ARBABI GHAHROUDI et al., 1997, FEBS Lett., 414:521-6). The amplified product of approximately 600 bp was subjected to a second round of PCR using either the primers VHBACKA4 and VHFOR36 or the primers VHBACKA4 and LH specific of the long hinge antibody (as described in International Application No. WO 2004/044204). The primers were complementary to the 5' and 3' ends of the amplified product and incorporated SfiI and NotI restriction sites at the ends of the VHH genes. The PCR products were digested and ligated into phage vector pHEN 1 (HOOGENBOOM and WINTER, 1992, above-cited). The resulting library was composed of two sublibraries, one derived from VHH DNA-encoding genes with no hinge and the other from long hinge antibody genes.

The VHH domain population was converted to ribosome display format using PCR and transcribed to mRNA as follows (MOURATOU et al., 2007, Proc Natl Acad Sci USA., 104:17983-8). Clones from the VHH domain population were amplified using the primer VHH-SPEF that contained a 5' extension containing the prokaryotic Shine-Dalgarno sequence and the primer VHH-SPER. The 400 bp PCR product was then amplified using a mixture of SDA-MRGS primer (5 µM), VHH-SPER primer (5 µM) and T7C primer (5 µM). The 450 bp product was purified with the Wizard® SV purification kit (Promega).

A peptide linker was added to ensure that the protein displayed on the ribosome was accessible to potential ligands. DNA encoding this linker, corresponding to a part of the *E. coli* protein TolA was PCR amplified by using the primers VHH-link and TolAkurz.

Finally the library was assembled with the TolA linker by PCR assembly using primers TolAkurz and T7B.

The final assembly product corresponded to a library of VHH with all of the 5' and 3' regions necessary to its use for ribosome display selections, as previously described (MOURATOU et al., 2007, see above).

Ribosome Display Selection Rounds

GFAP (10 µg/ml) was bound in a MaxiSorp™ plate (Nunc, Denmark) and selections by ribosome display were performed at 4° C. Selection was performed according to MOURATOU et al. (2007, see above). The wells were blocked with 300 µl 0.5% BSA in TBS for 1 hour at room temperature. Before the ribosome-display round, the wells were then extensively washed with washing buffer WBT (50 mM Tris acetic acid, pH7.5, 150 mM NaCl, 50 mm Mg $(CH3COO^-)_2$, 0.05% tween 20). A ribosome display round consisted of a 15 mn-prepanning step on a well coated with PBS and a 1 hour binding step on the target protein. After washing, RNA purification and reverse transcription (with primer VHH-SPER), a first PCR was done using the primers VHH-SPEF and VHH-SPER. This RT-PCR product was purified on an agarose gel and reamplified in a second PCR using T7C, SDA-MRGS and VHH-SPER primers. This PCR product was purified on an agarose gel and reamplified in a third PCR using T7B and TolAkurz primers. The third PCR product served as template for the next round of ribosome display. Three identical rounds of selection were performed to isolate high-affinity binders.

VHH Expression Either with a His-Tag or with a CH2 Domain, Allowing its Recognition by Anti-Tag or Anti-Alpaca Antibodies VHH Expression with a His-Tag in the pET System The coding sequence of the VHH was subcloned in vector pET 22 using the NcoI and NotI restriction sites according to the manufacturer's instructions (Novagen, Darmstadt, Germany). Transformed *E. coli* BL 21 (DE3) cells expressed VHHs in the periplasm after induction by IPTG 1 mM for 18 hours at 15° C. Periplasmic extracts were obtained by spheroplasting cells, suspended in 50 mM sodium phosphate buffer pH 8 containing 20% sucrose and 1 mM EDTA, and hydrolysing the peptidoglycan with 5 mg/ml lysozyme for 20 min at 4° C., in the presence of protease inhibitors (Complete™, Boehringer Mannheim, Germany). The suspension was then centrifuged 2 min at 10,000 rpm. The supernatant corresponding to the periplasmic extract was kept at 4° C. Purified VHHs were obtained by IMAC using a chelating agarose column charged with $Ni^{2+}$ (Superflow Ni-NTA, Qiagen Ltd, UK) according to manufacturer's instructions. Purified VHH were dialysed against PBS and the protein content was measured using the Bradford reagent. The purity of the final preparation was evaluated by SDS-PAGE with Coomassie staining and by Western blot.

Expression of VHH with the CH2 Domain

Anti-His tag antibodies may prove to be difficult to use in immunohistochemistry experiments. This is why VHHs coupled with the CH2 domain were also prepared. Specific and sensitive rabbit anti-alpaca antibodies directed against the CH2 domain are available (LAFAYE et al., 2009, Mol Immunol., 46:695-704). Secondary anti-rabbit antibodies conjugated with horseradish peroxidase are routinely used in Neuropathology laboratories. The alpaca Immunoglobulin CH2 domain was amplified by RT-PCR using primer CH2-Fwd-Not and CH2-Rev-Xho (LAFAYE et al., 2009, cited above). These primers contain respectively a NotI and a XhoI site allowing the cloning of CH2 domain in pET 22 vector in frame with VHH gene. The expression and purification of VHH were performed as described in LAFAYE et al., 2009 (cited above).

Nucleotide Sequencing

Nucleic acid sequences were determined using double-stranded DNA and the appropriate primers (LAFAYE et al., 1995, Res Immune., 146:373-82; Erratum in: Res Immunol., 1996, 147:61 and EHSANI et al., Plant Mol. Biol., 2003, 52:17-29).

Enzyme-Linked ImmunoSorbent Assay (ELISA)

A modified version of a standard ELISA was used to test for the presence of VHH in culture supernatants. Microtiter plates (Nunc, Denmark) were coated by incubation overnight at 4° C. with 5 µg/ml of antigen diluted in PBS. Plates were washed four times with buffer A (0.1% Tween 20 in PBS), and VHHs were diluted in buffer 13 (0.5% gelatin in buffer A). The plates were incubated for 2 hours at 37° C. and washed again, before adding a horseradish peroxidase-labeled rabbit anti-c-myc (A14) (Santa Cruz Biotechnology, Ca, USA) or with a rabbit anti-His tag antibody (Santa Cruz, Ca, USA). Then, the plates were washed with buffer A, and freshly prepared 0.2% orthophenylenediamine (Dakopatts A/S, Glostrup, Denmark), 0.03% $H_2O_2$ in 0.1 M citrate buffer, pH 5.2, were added to each well. The peroxidase reaction was stopped by adding 3 M HCl, and the optical density was measured at 490 nm.

Determination of Dissociation Constants by ELISA

The binding affinity of VHHs was determined as described by FRIGUET et al. (1985, J Immunol Methods, 77:305-319). Briefly, various concentrations of GFAP were incubated in solution overnight at 4° C. with a known quantity of VHH until equilibrium was reached. The VHH concentration had been determined by preliminary ELISA calibrations. 100 µl of solution was transferred to a well of a microtiter plate previously coated with GFAP and was incubated for 20 min at 4° C. The plates were washed with PBS-Tween 0.1%. VHHs were detected with rabbit anti-His tag antibodies (eBiosciences, San Diego, Calif.) followed by adding β-galactosidase-conjugated goat anti-rabbit Igs (Biosys, Compiègne, France) and 4-methylumbelliferyl β-D galactoside (Sigma Aldrich, Saint-Quentin Fallavier, France). Fluorescence was read at 460 nm, after excitation at 355 nm. $K_D$ was estimated from the slope of the regression curve obtained by plotting the reciprocal of the fraction of bound antibody versus the reciprocal of the molar concentration of antigen.

Polyacrylamide Gel Electrophoresis and Western Blot

Murine brain proteins (300 mg) were extracted in a potter with 600 µl of NuPage LDS sample buffer (Invitrogen) and kept for 10 mn at 70° C. An aliquot was diluted 1:10 (v/v) with the same sample buffer then treated at 70° C. for 10 min. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution. Immunoblotting of membranes was accomplished with the different VHHs, and revealed by peroxidase-labeled rabbit anti-His tag (Santa Cruz, Ca, USA) followed by peroxidase labeled goat anti-rabbit immunoglobulins. Finally, peroxidase activity was visualized using a chemiluminescent kit (Amersham).

2) Results

VHHs were amplified by PCR and three successive rounds of selection were performed. After the third round of selection, DNA was purified and cloned in the pET22 vector for periplasmic expression of soluble VHHs. Twenty clones were chosen for screening by ELISA and all of these clones bind specifically to GFAP. These clones have been sequenced and three sequences (VHH-E3, -E9 and -A10) have been obtained (FIG. 1). These sequences show slight differences suggesting that the specific immune response against GFAP is oligoclonal.

The nucleotide sequences encoding VHH-E3, -E9 and -A10 are listed in the herewith attached sequence listing as SEQ ID NO: 7, 10 and 4.

Yields of 1-2 mg of VHH/l of bacterial culture were obtained after immobilized metal affinity chromatography of periplasmic extracts. The single domain products were shown to be highly pure and homogenous by SDS-PAGE.

Figure 2:
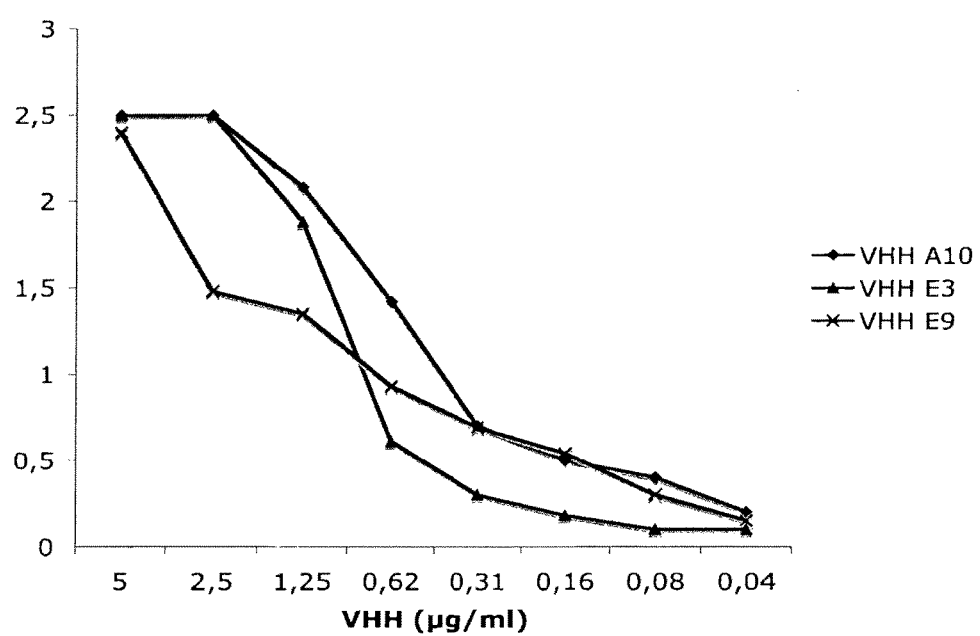
FIG. 2 shows the binding of the VHH domains VHH-A10, -E3 and -E9 to GFAP analysed by ELISA. Microtiter plates were coated with GFAP and various concentrations of VHH were added.
Figure 3:
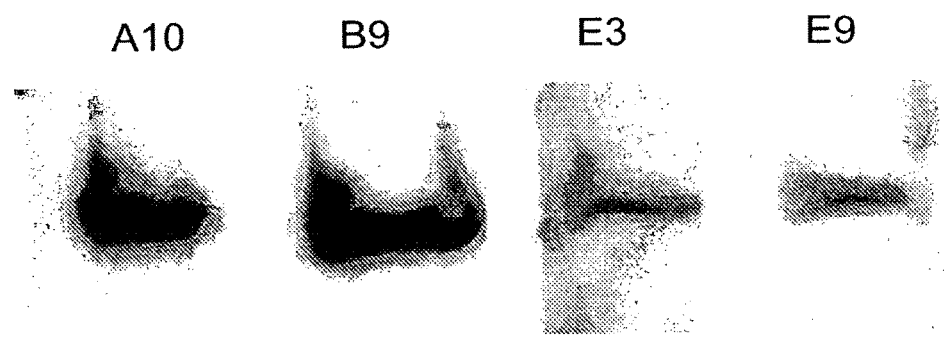
FIG. 3 shows the Western blot analyses of anti-GFAP specificities. Murine brain extracts were electrophoresed, immunoblotted and incubated with the VHH domains VHH-A10, -B8, -E3 and -E9.

The specificity of the different VHHs was tested by ELISA and by Western blot. All the VHHs were specific for GFAP by ELISA (FIG. 2) and could detect at least 40 ng of protein. A 46 Kda band corresponding to the size of GFAP was revealed on the immunoblots of murine brain extracts (FIG. 3).

VHH-A10 and VHH-E9 have an affinity of respectively $3.1 \cdot 10^{-9}$ M and $5.6 \cdot 10^{-9}$ M while VHH-E3 affinity is in the micromolar range.

EXAMPLE 2: VHH-A10 (SEQ ID NO: 5) RECOGNIZES GFAP ON MOUSE AND HUMAN BRAIN SECTIONS

1) Materials and Methods

Subjects

Human cortical brain tissue was obtained from the Hôpital Pitié-La Salpetrière, Paris, France.

Female Balb/C mice, 6 to 8 weeks old, were euthanized with sodic pentotbarbital (Ceva), and brains were fixed by intra-aortic perfusion of 200 ml 4% paraformaldehyde in PBS.

Immunocytochemistry

Mice were killed with sodium pentobarbital (Ceva). Brains were fixed by intra-aortic perfusion of 200 ml 4% paraformaldehyde in PBS. The free-floating sections method was used for the immunolabelling. Vibratome sections obtained from the fixed brains were treated successively for: neutralization of free aldehydes remaining in the tissues, neutralization of endogenous peroxidases, saturation of non-specific binding sites, and permeabilization of cells in the nervous tissue with Triton as the detergent.

Immunostaining of human brain tissue was performed on 5 µm thick paraffin sections. Sections were de-paraffinized in xylene, rehydrated through ethanol (100%, 96%, and 90%) and finally brought to water. They were incubated with 3% hydrogen peroxyde and 20% methanol, to quench for endogenous peroxydases, and washed in water. Non-specific binding was blocked by incubating the sections for 10 minutes in 2% bovine serum albumin in TBS plus 0.5% Tween.

Appropriate dilutions of primary antibodies were applied overnight in a humidified chamber at room temperature (typically 1 µg/ml for VHH, and 1:200 for rabbit-anti GFAP polyclonal antibodies). Slides were washed with TBS-Tween and incubated with secondary antibodies (rabbit anti-His Tag or rabbit anti alpaca immunoglobulin) in TBS-Tween at room temperature for 2 hours. Slides were then incubated with peroxidase goat anti-rabbit immunoglobulins, and developed with diaminobenzidine (DAB) for 2 minutes. After washing with TBS-Tween, slides were counter-stained with haematoxylin.

Double Labeling

Paraffin sections of human samples were pretreated as previously. They were left overnight in a solution containing the anti-GFAP VHH and a mouse anti-GFAP monoclonal antibody at the appropriate dilutions in a humidified chamber at room temperature (1 µg/ml for anti-GFAP VHH, and 1:500 for mouse anti-GFAP monoclonal antibodies M0756, Dako). Slides were washed with TBS-Tween and incubated for 2 hours in a TBS-Tween solution containing rabbit anti-His Tag (1:300) at room temperature. The slides were then incubated in a solution of goat anti-rabbit and goat anti-mouse immunoglobulins coupled respectively with CY2 and CY3 (Cy2 AffiniPure F(ab')2 Fragment Goat Anti-Rabbit IgG, Cy3 AffiniPure F(ab')2 Fragment Goat Anti-Mouse IgG, all from Jackson ImmunoResearch), washed in TBS-Tween, dehydrated and mounted in Mowiol.

Diffusion Analysis of VHH and mAb

Blocks of the frontal cortex were sliced with a vibratome at 70 µm of thickness. The sections were pretreated with 3% hydrogen peroxide for 30 min at room temperature. They were permeabilized and blocked in a PBS solution containing 0.1% Triton X-100 (PBST), 2% bovine serum albumin and 5% normal goat serum for 30 min at room temperature. The sections (covering an area of approximately 4 $cm^2$) were mounted between two coverslips and left for the night in the solution of the primary antibody (VHH-His, 1 µg/ml in PBS or monoclonal mouse Anti-GFAP antibody, 1:500). Coverslips were used to limit the diffusion to the edges of the section by preventing contact of the primary antibody with the 2 sides of the section (the technique is disclosed by GABBOT and SOMOGYI (1984, J Neurosci Methods, 11:221-230).

Coverslips adhesion was obtained by the removal of excess solution and of air bubble. After incubation during the night, one of the coverslips was gently taken off by slowly rotating a cutter blade interposed in the space that separates them. The following steps were performed on the free floating sections. A rabbit anti-His antibody, at a dilution of 1:10 000, was used to revealed the VHH. The rabbit anti-His antibody or the mouse anti-GFAP antibody were revealed by Dako REAL™ System Kit (peroxidase/DAB). The sections were dehydrated through graded ethanol (70%, 90%, and 100%) and xylene. They were mounted in DPX Neutral mounting medium.

Statistical Analysis

The distance between the pia matter and the deepest immunostained astrocyte ("diffusion distance") was evaluated 18 times in 4 sections. The mean diffusion distances were calculated for the mouse mAb and the llama VHH. The diffusion distances were compared by a Student t test as pairs VHH/mAb immunohistochemistry at the same location of mirror sections (N=18).

2) Results

Figure 4:
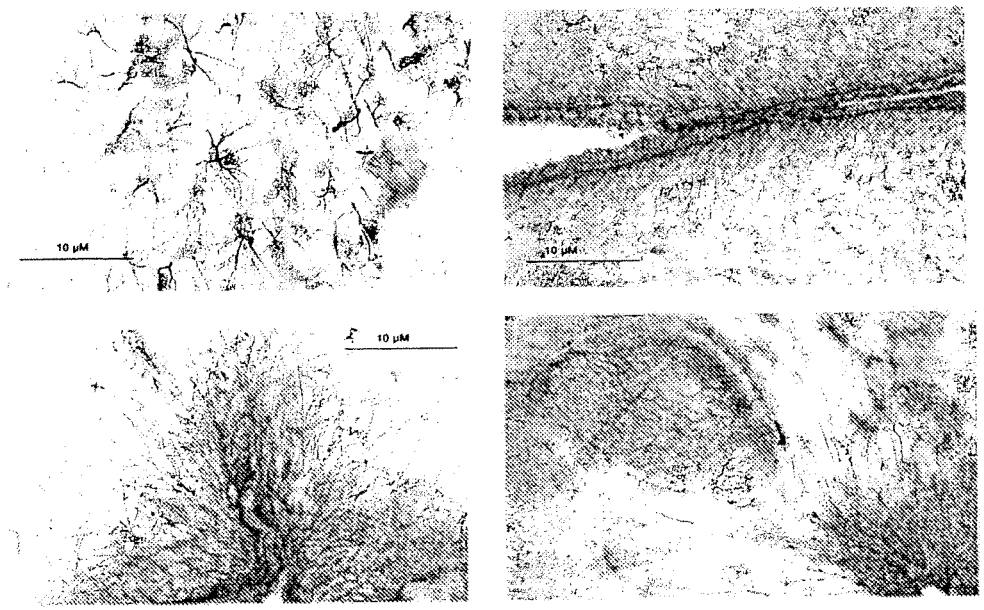
FIG. 4 shows the immunolabelling of the GFAP in astrocytes of murine brain sections. The brain sections were fixed and permeabilized before exposure to VHH-A10.

The distribution of VHH-specific immunoreactivity in mouse and human brains sections were examined after aldehyde fixation and membranes permeabilization, using standard procedure for immunostaining. Immunohistochemistry experiments were performed with VHH-A10 (SEQ ID NO: 5) or VHH domain of SEQ ID NO: 3 fused in frame with the Ig CH2 domain and the His tag (SEQ ID NO: 29) were both used. With this construction, the signal could be amplified by using rabbit anti-alpaca Ig polyclonal antibodies as secondary antibodies, in turn labelled by an anti-rabbit goat polyclonal antibody. As previously reported (LAFAYE et al, 1995, above-cited), the results obtained were similar with the His-tagged antibody. VHH-A10 revealed a strong immunoreactivity in astrocytes. GFAP-positive astrocytes were seen in mouse brain mostly in the glia limitans and in the white matter. Only very few astrocytes were observed in grey matter (FIG. 4).

Immunolabeling in Human Brain:

VHH-A10 fused with the CH2 domain immunolabeled astrocytes in human brain sections from controls and Alzheimer patients (FIGS. 5 and 6, respectively) as well as in sections from gliomas (FIG. 7).

Normal Cortical Samples:

Fibrous GFAP positive astrocytes were seen in the white matter and in the subpial region. The labeling was strong in the processes and in the cell body close to the plasma membrane while the perinuclear region was not labeled (FIG. 5). GFAP positive astrocytes were sparse in the cortex itself, at a distance from the pia matter, and their processes were only lightly labeled. They were equally rare in the pyramidal fields of the hippocampus except in the CA4 sector and in the dentate gyrus. Vessels (capillaries, veins and arteries) were covered by GFAP positive astrocytic feet (FIGS. 5 c and d). A few neurons appeared to be embraced by positive fibers.

Alzheimer Disease Samples:

The number of positive astrocytes was much larger in the samples from Alzheimer patients. This was particularly striking in the grey matter of the isocortex and hippocampus. The processes were numerous and strongly labeled. These processes circumscribed senile plaques (FIG. 6). They pervaded extracellular (ghost) neurofibrillary tangles. Numerous neurons were embraced by GFAP positive fibers.

Astrocytoma Samples:

Cellular body and processes of reactive and tumoral binucleated astrocytes were labeled (FIGS. 7 a and b). Protoplasmic astrocytes were observed in the areas that bordered necrosis (FIGS. 7 c and d).

Double Labelling with a Mouse Anti-GFAP mAb and VHH-A10

Colocalisation was seen in almost all the immunolabeled astrocytes (FIG. 8). A few were only labeled by VHH-A10; none was only labeled by the mouse mAb. In the processes, some short segments appeared only labeled by one of the two antibodies, the mouse mAb more often in the proximal part of the processes, the VHH-A10 more often in its distal and thin part. Colocalization was observed in the astrocytic feet.

VHH-A10 Diffuses More Efficiently in Tissues than Anti-GFAP mAb

Astrocytes were labelled with each one of the two antibodies in two sequential sections. Diffusion distance (over a period of 8 hours) was 196±17 µm (mean±SEM) for mAb and 422±24 µm for VHH-A10 (i.e.; 24.5 µm/hour and 52.75 µm/hour respectively). The mean difference was 226 µm (=28.25 µm/h), N=18, t=9.3 and p<0.0001) (FIG. 9). In other words the diffusion distance was roughly twice longer for VHH-A10 than for mAb.

EXAMPLE 3: STEREOTAXIC, INTRANASAL OR INTRAVENOUS ADMINISTRATION OF VHH-A10 (SEQ ID NO: 5)

1) Materials and Methods

Stereotaxic and Intranasal or Intravenous Administration of VHH

Female Balb/C mice, 6 to 8 weeks old, were used for subsequent experiments. Before the stereotaxic and intranasal administration, mice were anesthesized with a single intra-peritoneal administration of a mixture of ketamine hydrochloride (Imalgen) and xylazine (Rompun).

For stereotaxic injection, mice were positioned on a stereotaxic frame (Kopf). Through a hole drilled in the cranium, a metallic canula was positioned into the rostrodorsal striatum (x=1.3(±0.2) mm; y=Bregma+1.54; z=~3; PAXINOS and FRANKLIN, The mouse Brain in Stereotaxic Coordinates, Compact 2nd edition, Elsevier Academic Press, San Diego, 2004). Using a Harvard pump, 3 µl of VHH (1 mg/ml) were injected into the striatum at a rate of 0.2 µl/min. Penetration of the VHH was then allowed for 4, 7.5, or 14 hours before euthanasia and perfusion as described above in the method for immunohistochemistry.

For nasal instillation, VHH (1 mg/ml) were placed in the nostril using a gel-loading tip. Each mouse received a total of 40 µg in 10 µl drops to alternating nares every 2-3 min. Penetration of the VHH was then allowed for time ranging from 1 to 24 hours before euthanasia and perfusion.

2) Results

Intracranial Stereotaxic Administration of VHH Labels Astrocytes

In this experiment, the VHH-A10 was first stereotaxically injected into the live rostro-dorsal striatum. It was allowed to diffuse in the cerebral tissue before processing for the aldehydic perfusion followed by the standard procedure for its immunostaining. The injected VHH showed diffuse distribution through the striatum 5 hours after the stereotaxic injection (FIG. 10). After 7 hours, the diffusion pattern of VHH remained broad and immunolabelled astrocytes were observed in the white matter. After 14 hours, the immuno labelling of white matter was more intense and glia limitans was also stained.

Intranasal Administration of VHH Labels Astrocytes

In this experiment, the VHH-A10 was administratted to the live brain tissue before histological treatments. Intranasal instillation of 40 µg of VHH resulted in significant staining of astrocytes throughout the CNS (FIG. 11). At 1 hr after nasal instillation, the olfactory bulb was heavily stained with a significant immunoreactivity in the glia limitans and in the white matter (FIG. 11). The glia limitans located at the surface of the cerebral cortex was also labelled. At 3 hr post-instillation, the immunostaining in the glia limitans was faint. No staining was observed at 6 hr-, 12 hr- and 24 hr-after the nasal instillations.

EXAMPLE 4: VHH-E9 CROSSES THE BLOOD BRAIN BARRIER AND LABELS SPECIFICALLY GFAP

1) Materials and Methods

Obtaining, Purification and Characterization of VHH-E9

The expression and purification of anti-GFAP VHH-E9 was performed according to Example 1 above. SDS-PAGE was performed using NuPAGE Novex 4-12% Bis-tris gel according to manufacturer's instructions (Invitrogen). Western blotting were performed according to Example 1 above.

Isoelectric focusing was performed using PhastSystem with PhastGel IEF 3-9. The pI Calibration Kit (Biorad) was used as standards. The pI calculation of the VHHs has been performed using EMBOSS iep software (at SOURCE-FORGE).

The heat denaturation of VHH-E9 was adapted to the method described in OLICHON et al. (2007, BMC Biotechnol., 7:7). VHHs are re-suspended in PBS/NaCl 300 mM and are heated for 15 minutes at 75° C. then cooled down at 4° C. for 20 minutes. The binding affinity of VHHs was determined by ELISA as described in Example 1 above.

Site-Directed Mutagenesis

The Quick change site directed mutagenesis kit (Stratagene) was used. The mutagenesis was performed according to manufacturer's instructions/with the following primers:

```
Mutations of cysteine 22;
-E9C22Ssens (SEQ ID NO: 30):
5'-GGGTCTCTGAGACTCTCCTCTGCAGCCTC1GG-3'

-E9C22Srev (SEQ ID NO: 31):
5'-CCAGAGGCTGCAGAGGAGAGTCTCAG-3'

Mutations of cysteine 96
-E9C96Ssens (SEQ ID NO: 32):
5'-CTACCTTGTTGCGTGATCGCAGAGTAATACACGGCCGT-3'

-E9C96Srev (SEQ ID NO: 33):
5'-ACGGCCGTGTATTACTCTGCGATCACGCAACAAGGTAGC-3'
```

The plasmids containing the VHH were sequenced by ATGC using T7 promoter and T7 terminator primers.

Transport Across a Blood Brain Barrier In Vitro Model

Immortalized human brain endothelial cells hCMEC/D3 have been previously described in detail by WEKSLER et al. (2005, The FASEB Journal, 19:1872-1874). Cell viability in the presence of VHH was assessed by MTT assay. The permeability of hCMEC/D3 cell monolayers to VHH was measured on transwell polycarbonate insert filters (pore size 3 µm, Corning, Brumath, France). hCMEC/D3 cells were seeded on the filters at a confluent density of $2 \times 10^5$ cells/cm$^2$ in EGM-2 medium. Transport studies were performed at 3 days post-seeding. Experiments were initiated by adding VHH to the upper chamber containing either collagen, coated inserts without cells, hCMEC/D3 cells or hCMEC/D3 cells pre-exposed to various pharmacological modulators for 30 min. Transport studies were conducted at 37° C. The lower chamber was sampled at various time intervals (10, 30 and 60 min) and the presence of VHH was determined by ELISA and Western Blot.

Immunohistochemistry on Histological Sections

Adult females C57B16 mice were euthanized with sodium pentobarbital i.p. (Ceva). Brains were fixed by intra-aortic perfusion with 150 ml 4% paraformaldehyde in PBS 0.1M pH 7.4, and postfixed in the same fixative overnight at 4° C.

Vibratome sections, 70 µm in thickness, were collected in PBS 0.1M, pH 7.4. Free floating brain sections were treated to neutralize free aldehydes, endogenous peroxidases, and non-specific binding sites, prior to immunolabeling. The primary antibody VHH, diluted 1 µg/ml in PBS with 1% BSA, 1% normal goat serum, and 0.1% Triton-X100, was incubated overnight at 4° C. In the sections the VHH were decorated, successively, with rabbit anti-His tag antibodies (eBiosciences, USA) overnight at 4° C., then at room temperature with goat biotinylated anti-Rabbit IgG(H+L) (Vector BA-1000) for 2 hours, and ABC complex (Vector) for 30'. DAB was used as chromogen. Sections were collected on superfrost glass slides, dehydrated in graded ethanol solutions, and mounted in DPX neutral mounting medium (Aldrich).

Carotidian Injections of VHH In Vivo

Before intra-carotidian injections, mice were anesthetized with a single intra-peritoneal administration of a ketamine hydrochloride (Imalgen) and xylazine (Rompun) mixture.

The common carotid arteries were exposed with the aid of a microscope and cannulated with fine silicon tubing (PP25× 100FT, Portex, UK). The perfusion fluid containing VHH was infused in the carotid at a constant rate by a peristaltic pump (Model PHD 2000, Harvard apparatus, Harvard, Mass.). Some animals were transiently perfused with mannitol 30% (200 µl for 30 s) to disrupt the BBB (RAPOPORT et al., 1980, American Journal of Physiology, 238:R421-R431), prior to the injection of VHH. Allowing diverse times for intra-tissular diffusion, the mice were then perfused. The presence of the VHH-His$_6$ putative intrabody in the cerebral tissue was detected using the standard immunohistochemical procedure described above.

Parasite infection: A central feature of Cerebral Malaria pathology after infection with *Plasmodium berghei* ANKA line is the alteration and opening of the BBB (BEGHDADI et al., 2008, Journal of Experimental Medicine, 205:395-408). C57/B16 mice were inoculated i.p. with $10^6$ infected erythrocytes Pb ANKA per mice. At day 5 after infection, mice were injected with VHH via the carotide artery.

2) Results

Characterization of VHH-E9

A single 46 Kda band corresponding to the size of GFAP were revealed on the immunoblots of murine brain extracts (see FIG. 12).

The pI of VHH-E9 was determined by isoelectric focusing (IEF) (see FIG. 12) and calculated using IEP software. The pI was found to be 8.72 and 9.15, respectively for VHH-E9 with or without the His tag.

The labeling of GFAP in murine astrocytes using standard immunohistochemical procedure on free floating brain sections was analyzed. GFAP-positive astrocytes were seen mostly in the white matter, hippocampus, glia limitans, and some in the gray matter of the cerebral cortex (FIG. 13).

The affinity of VHH-E9 heated at 75° C. for 15 minutes, was measured at $3.8 \cdot 10^{-9}$ M, suggesting that VHH-E9 is thermostable.

Capacity of VHH-E9 to Cross the BBB In Vitro

The capacity of VHH-E9 to cross the BBB, was tested in the in vitro BBB model developed by WEKSLER et al. (2005, The FASEB Journal, 19:1872-1874), using a monolayer of hCMEC/D3 cells. VHH-E9 was not toxic to these cells even at very high concentration (1 mg/ml). The upper chamber received 10-20 µg/ml of VHH-E9 and the rate of passage of VHH-E9 from the luminal to the abluminal side of the monolayer was measured.

FIG. 14A illustrates the transcytosis of functional VHH-E9. This time-dependent passage reaches a maximum at 30 min, and after 60 min about 1-5% of VHHs are present in the lower chamber.

It is now agreed that ionic interactions between cationic proteins and negative charges present on cell membranes trigger an adsorptive-mediated endocytosis (AME) (VORBRODT, 1989, Journal of Neurocytology, 18:359-368). The contribution of AME to VHH-E9 transcytosis was then assessed. HCMEC/D3 were preincubated for 30 mn either with highly cationic protamine sulfate (40 µg/ml) or polylysine (300 µM), both previously shown to inhibit AME, prior to assessing VHH-E9 uptake and transport. Both cationic peptides inhibit the transendothelial migration of VHH-E9 suggesting that the transmigration is charge-dependant (FIG. 14B). To investigate whether VHH-E9 is internalized and transported by macropinocytosis, VHH transmigration was tested in the presence of 500 µM amiloride, which inhibits the formation of macropinosomes. Amiloride had an inhibitory effect on transendothelial migration of VHH-E9 (FIG. 14B).

These observations strongly suggest that VHH-E9 is transported through the endothelial cell monolayer by an intracellular endocytic mechanism rather than via intercellular pathway.

Capacity of VHH-E9 to Cross the BBB In Vivo

VHH-E9 was then tested in vivo for its ability to cross the BBB, in both normal and pathological conditions. Different amounts of VHH-E9 were injected via the left carotide of untreated mice, during 60 minutes. One mouse received 200 µl of VHH-E9 at the concentration of 2 mg/ml (0.4 mg); a second one received 200 µl of VHH-E9 at the concentration of 20 mg/ml (4 mg); a third one received 500 µl of VHH-E9 at the concentration of 50 mg/ml (25 mg). After the injection, the diffusion of VHH-E9 in the cerebral tissue was allowed for 1 hour before mice were euthanized and perfused with fixative. Immunostaining of astrocytes were observed only with mice that received 4 mg and 25 mg of VHH-E9 (FIG. 15). The staining pattern was similar in the 2 mice and was slightly more intense in mice receiving 25 mg of VHH. This staining was localized in astrocytic feet surrounding blood vessels, astrocytes present in the white matter (FIGS. 15 A, B), the hippocampus (FIG. 15 C), pial surface (FIG. 15 D), gray matter (FIG. 15 E), and olfactif bulb (FIG. 15 F). This staining was more intense in the left hemisphere, ipsilateral to the injected carotid, as compared to the right one (FIG. 15 G). 4 mg of VHH was also injected for 60 min and mice were perfused either 90 minutes or 4 hours later. Staining was similar in the 60 and 90 min mice and reduced after 4 hours.

Pathological opening of the BBB observed in neurological (inflammatory, infectious, neoplasic) and neurodegenerative diseases, allows circulation of plasma, electrolytes, drugs, proteins, blood cells, into the cerebral tissue, with detrimental effects. The ability of VHH-E9 to go through altered BBB was investigated using either osmotic stress or cerebral malaria. The tight junctions of the cerebrovascular endothelium can be reversibly opened, in vivo, under osmotic stress. 250 µl of an hypertonic solution of mannitol 30% was injected for 30 seconds in the carotid, prior to injection of 200 µl of VHH-E9 at the concentration of 2 mg/ml, for 60 min. Significant staining of astrocytes was observed throughout the CNS (FIG. 16).

Cerebral malaria, a clinically complex syndrome of coma and encephalopathy, is correlated with the rupture of BBB integrity. In an experimental model, C57BL/6 mice developed similar neuropathological signs, five days after i.v. injection of *Plasmodium berghei* ANKA infected erythrocytes (BEGHDADI et al., 2008, Journal of Experimental Medicine, 205:395-408). Intracarotidian injection of 200 µl VHH-E9 (2 mg/ml) (400 µg) during 60 min, in two infected mice, resulted in significant staining of astrocytes (FIG. 17), in the olfactive bulb (FIG. 17A), white matter (FIG. 17B), hippocampus (FIG. 17C), and the "caudal" region of the brain (FIG. 17). Again, immunostaining was more intense in the left hemisphere, ipsilateral to the VHH-E9 injected carotid, as compared to the right one (FIG. 17E). In both osmotic stress and cerebral malaria conditions, 400 µg of VHH-E9 is sufficient to label astrocytes, as compared to 4 mg needed when BBB is intact. It was then demonstrated that VHH-E9 diffuses and remains active in cerebral tissue under pathological conditions.

Characterization of VHH-E9 SS-Free

A fully functional cysteine-free derivative of VHH E9 was generated by replacing the disulfide forming cysteine residues (Cys 22 and Cys 96) with the amino acid combination serine-serine. VHH-E9 SS-free had an affinity of $12 \cdot 10^{-9}$ M, only reduced twice compared to the affinity of native VHH-E9, suggesting that the antigen binding properties were not affected by removal of disulfide bonds.

CONCLUSION

The capacity of GFAP specific-VHHs to act as transbodies and intrabodies in vitro as well as in vivo has been demonstrated. These transbodies need to fulfill a set of requirements not observed with conventional antibodies and corresponding fragments; namely: 1) they cross the BBB, 2) diffuse in brain tissues, 3) penetrate into cells, 4) are intracellularly stable, and 5) bind specifically to intracellular antigens. Once GFAP specific-VHH has penetrated into the cells, it specifically labels GFAP, suggesting that it remains active in spite of the reducing properties of the cytosol.

Antibody domains carry an internal disulfide bond, which connects both β-sheets of the β-sandwich structure and is strictly conserved during evolution, witnessing its important contribution to their stability (ALZARI et al., 1988, Annual Review of Immunology, 6:555-580; PROBA et al., 1997, Journal of Molecular Biology, 265:161-172). Genetic removal of the disulfide bonds in the variable domains of antibody fragments (Fab, Fv or scFv) yields no functional protein, suggesting a severe loss of stability. Normal antibody fragments do not form disulfide bonds in the cytoplasm and usually are unable to achieve a stable native folding in the absence of the disulfide bonds (BIOCCA et al., 1995, Bio/Technology, 13:1110-1115).

VHHs directed against a GFAP make them interesting agents for brain imaging and new therapeutic strategies to target intracerebral antigens such as amyloid proteins, to reach intracerebral tumor cells, or to cure infections caused by viruses, bacteria or parasites.

The invention claimed is:

1. A method for screening a composition for transmigration across the blood-brain barrier (BBB) comprising:
   providing a composition comprising a substance of interest linked to a VHH antibody comprising an amino acid sequence selected from the group consisting of the consensus amino acid sequence SEQ ID NO: 1, SEQ ID NO: 3, SEQ ID NO: 6, and SEQ ID NO: 12;
   administering the composition to a mammal; and
   determining that the composition has crossed the BBB by detecting the presence of the VHH antibody on the cerebral side of the BBB.

2. The method of claim 1, wherein the mammal is a human.

3. The method of claim 1, wherein the composition is administered by intranasal, intravenous, intraperitoneal, intramuscular, or subcutaneous injection.

4. The method of claim 1, wherein the VHH antibody is directed against a glial fibrillary acidic protein (GFAP).

5. The method of claim 1, wherein the substance of interest is a fluorophore, a heavy metal chelate, or a radioisotope.

6. The method of claim 1, wherein the substance of interest is an enzyme.

7. The method of claim 1, wherein the isoelectric point of the VHH is calculated using a computer program.

8. A method for screening a composition for transmigration across the blood-brain barrier (BBB) comprising:
   providing a composition comprising a substance of interest linked to a VHH antibody comprising an amino acid sequence selected from the group consisting of the consensus amino acid sequence SEQ ID NO: 1, SEQ ID NO: 3, SEQ ID NO: 6, and SEQ ID NO: 12;
   administering the composition to a mammal; and
   determining that the composition has crossed the BBB by detecting the presence of the substance of interest on the cerebral side of the BBB.

9. The method of claim 8, wherein the mammal is a human.

10. The method of claim 8, wherein the composition is administered by intranasal, intravenous, intraperitoneal, intramuscular, or subcutaneous injection.

11. The method of claim 8, wherein the VHH antibody is directed against a glial fibrillary acidic protein (GFAP).

12. The method of claim 8, wherein the substance of interest is a fluorophore, a heavy metal chelate, or a radioisotope.

13. The method of claim 8, wherein the substance of interest is an enzyme.

14. The method of claim 8, wherein the isoelectric point of the VHH is calculated using a computer program.

\* \* \* \* \*

SEQUENCE LISTING

<160> NUMBER OF SEQ ID NOS: 33

<210> SEQ ID NO 1

```
<211> LENGTH: 118
<212> TYPE: PRT
<213> ORGANISM: Lama pacos
<220> FEATURE:
<221> NAME/KEY: VARIANT
<222> LOCATION: (5)..(5)
<223> OTHER INFORMATION: /replace = Arg
<220> FEATURE:
<221> NAME/KEY: VARIANT
<222> LOCATION: (6)..(6)
<223> OTHER INFORMATION: /replace = Ala
<220> FEATURE:
<221> NAME/KEY: VARIANT
<222> LOCATION: (25)..(25)
<223> OTHER INFORMATION: /replace = Ser
<220> FEATURE:
<221> NAME/KEY: VARIANT
<222> LOCATION: (69)..(69)
<223> OTHER INFORMATION: /replace = Thr
<220> FEATURE:
<221> NAME/KEY: VARIANT
<222> LOCATION: (93)..(93)
<223> OTHER INFORMATION: /replace = Val
<220> FEATURE:
<221> NAME/KEY: VARIANT
<222> LOCATION: (107)..(107)
<223> OTHER INFORMATION: /replace = Gln
<220> FEATURE:
<221> NAME/KEY: VARIANT
<222> LOCATION: (108)..(108)
<223> OTHER INFORMATION: /replace = Glu

<400> SEQUENCE: 1

Asp Val Gln Leu Gln Val Ser Gly Gly Gly Leu Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala
        115

<210> SEQ ID NO 2
<211> LENGTH: 126
<212> TYPE: PRT
<213> ORGANISM: Artificial
<220> FEATURE:
<223> OTHER INFORMATION: VHH consensus sequence fused to an His tag
<220> FEATURE:
<221> NAME/KEY: VARIANT
<222> LOCATION: (5)..(5)
<223> OTHER INFORMATION: /replace = Arg
<220> FEATURE:
<221> NAME/KEY: VARIANT
<222> LOCATION: (6)..(6)
<223> OTHER INFORMATION: /replace = Ala
<220> FEATURE:
<221> NAME/KEY: VARIANT
<222> LOCATION: (25)..(25)
<223> OTHER INFORMATION: /replace = Ser
<220> FEATURE:
<221> NAME/KEY: VARIANT
```

```
<222> LOCATION: (69)..(69)
<223> OTHER INFORMATION: /replace = Thr
<220> FEATURE:
<221> NAME/KEY: VARIANT
<222> LOCATION: (93)..(93)
<223> OTHER INFORMATION: /replace = Val
<220> FEATURE:
<221> NAME/KEY: VARIANT
<222> LOCATION: (107)..(107)
<223> OTHER INFORMATION: /replace = Gln
<220> FEATURE:
<221> NAME/KEY: VARIANT
<222> LOCATION: (108)..(108)
<223> OTHER INFORMATION: /replace = Glu

<400> SEQUENCE: 2

Asp Val Gln Leu Gln Val Ser Gly Gly Gly Leu Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala Leu Glu His His His His His
        115                 120                 125

<210> SEQ ID NO 3
<211> LENGTH: 118
<212> TYPE: PRT
<213> ORGANISM: Lama pacos

<400> SEQUENCE: 3

Asp Val Gln Leu Arg Ala Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ile Thr Gln Gln Gly Ser Gly Arg Gly Gln Glu Thr Gln Val Thr
            100                 105                 110

Val Ser Ser Ala Ala Ala
        115

<210> SEQ ID NO 4
<211> LENGTH: 381
<212> TYPE: DNA
<213> ORGANISM: Artificial
<220> FEATURE:
```

<223> OTHER INFORMATION: VHH domain fused to a His tag
<220> FEATURE:
<221> NAME/KEY: CDS
<222> LOCATION: (1)..(381)

<400> SEQUENCE: 4

```
gat gtc cag ctg cgg gcg tct gga gga ggc tta gtg cag cct ggg ggg     48
Asp Val Gln Leu Arg Ala Ser Gly Gly Gly Leu Val Gln Pro Gly Gly
1               5                   10                  15 tct ctg aga ctc tcc tgt gca gcc tct gga ttc acc ttc agt aac tat     96
Ser Leu Arg Leu Ser Cys Ala Ala Ser Gly Phe Thr Phe Ser Asn Tyr
            20                  25                  30 gcc atg tac tgg ctc cgc cag gct cca gga aag gga atc gag tgg gtc    144
Ala Met Tyr Trp Leu Arg Gln Ala Pro Gly Lys Gly Ile Glu Trp Val
        35                  40                  45 tcg cgt att ggc cct ggt gga agt cac acc gag tat gca gac tcc gtg    192
Ser Arg Ile Gly Pro Gly Gly Ser His Thr Glu Tyr Ala Asp Ser Val
    50                  55                  60 aag ggc cga ttc acc atc tcc aga gac aac gcc aag aac acg ctg tct    240
Lys Gly Arg Phe Thr Ile Ser Arg Asp Asn Ala Lys Asn Thr Leu Ser
65                  70                  75                  80 ctg caa atg aac agc ctg aaa cct gag gac acg gcc gtg tat tac tgt    288
Leu Gln Met Asn Ser Leu Lys Pro Glu Asp Thr Ala Val Tyr Tyr Cys
                85                  90                  95 gcg atc acg caa caa ggt agc ggc cgg ggc cag gag acc cag gtc acc    336
Ala Ile Thr Gln Gln Gly Ser Gly Arg Gly Gln Glu Thr Gln Val Thr
            100                 105                 110 gtc tcc tca gcg gcc gca ctc gag cac cac cac cac cac cac tga        381
Val Ser Ser Ala Ala Ala Leu Glu His His His His His His
        115                 120                 125
```

<210> SEQ ID NO 5
<211> LENGTH: 126
<212> TYPE: PRT
<213> ORGANISM: Artificial
<220> FEATURE:
<223> OTHER INFORMATION: Synthetic Construct

<400> SEQUENCE: 5

```
Asp Val Gln Leu Arg Ala Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ile Thr Gln Gln Gly Ser Gly Arg Gly Gln Glu Thr Gln Val Thr
            100                 105                 110

Val Ser Ser Ala Ala Ala Leu Glu His His His His His His
        115                 120                 125
```

<210> SEQ ID NO 6
<211> LENGTH: 118
<212> TYPE: PRT
<213> ORGANISM: Lama pacos

<400> SEQUENCE: 6

Asp Val Gln Leu Gln Val Ser Gly Gly Gly Ser Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala
        115

<210> SEQ ID NO 7
<211> LENGTH: 381
<212> TYPE: DNA
<213> ORGANISM: Artificial
<220> FEATURE:
<223> OTHER INFORMATION: VHH domain fused to a His tag
<220> FEATURE:
<221> NAME/KEY: CDS
<222> LOCATION: (1)..(381)

<400> SEQUENCE: 7 gat gtc cag ctg cag gtg tct gga gga ggc tcg gtg cag ccg ggg ggg     48
Asp Val Gln Leu Gln Val Ser Gly Gly Gly Ser Val Gln Pro Gly Gly
1               5                   10                  15 tct ctg aga ctc tcc tgt gca gcc cct gga ttc acc ttc agt aac tat     96
Ser Leu Arg Leu Ser Cys Ala Ala Pro Gly Phe Thr Phe Ser Asn Tyr
            20                  25                  30 gcc atg tac tgg ctc cgc cag gct cca gga aag gga atc gag tgg gtc    144
Ala Met Tyr Trp Leu Arg Gln Ala Pro Gly Lys Gly Ile Glu Trp Val
        35                  40                  45 tcg cgt att ggc cct ggt gga agt cac acc gag tac gca gac tcc gtg    192
Ser Arg Ile Gly Pro Gly Gly Ser His Thr Glu Tyr Ala Asp Ser Val
    50                  55                  60 aag ggc cga ttc gcc atc tcc aga gac aac gcc aag aac acg ctg tct    240
Lys Gly Arg Phe Ala Ile Ser Arg Asp Asn Ala Lys Asn Thr Leu Ser
65                  70                  75                  80 ctg caa atg aac agc ctg aaa cct gag gac acg gcg tat tac tgt        288
Leu Gln Met Asn Ser Leu Lys Pro Glu Asp Thr Ala Ala Tyr Tyr Cys
                85                  90                  95 gcg atc acg caa caa ggt agc ggc cgg ggc cgg ggg act caa gtc acc    336
Ala Ile Thr Gln Gln Gly Ser Gly Arg Gly Arg Gly Thr Gln Val Thr
            100                 105                 110 gtc tcc tca gcg gcc gca ctc gag cac cac cac cac cac cac tga        381
Val Ser Ser Ala Ala Ala Leu Glu His His His His His His
        115                 120                 125

<210> SEQ ID NO 8
<211> LENGTH: 126
<212> TYPE: PRT
<213> ORGANISM: Artificial
<220> FEATURE:
<223> OTHER INFORMATION: Synthetic Construct

<400> SEQUENCE: 8

Asp Val Gln Leu Gln Val Ser Gly Gly Gly Ser Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala Leu Glu His His His His His
        115                 120                 125

<210> SEQ ID NO 9
<211> LENGTH: 118
<212> TYPE: PRT
<213> ORGANISM: Lama pacos

<400> SEQUENCE: 9

Asp Val Gln Leu Gln Val Ser Gly Gly Gly Ser Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ile Thr Gln Gln Gly Ser Gly Arg Gly Gln Gly Thr Gln Val Thr
            100                 105                 110

Val Ser Ser Ala Ala Ala
        115

<210> SEQ ID NO 10
<211> LENGTH: 381
<212> TYPE: DNA
<213> ORGANISM: Artificial
<220> FEATURE:
<223> OTHER INFORMATION: VHH domain fused to a His tag
<220> FEATURE:
<221> NAME/KEY: CDS
<222> LOCATION: (1)..(381)

<400> SEQUENCE: 10 gat gtc cag ctg cag gtg tct gga gga ggc tcg gtg cag cct ggg ggg     48
Asp Val Gln Leu Gln Val Ser Gly Gly Gly Ser Val Gln Pro Gly Gly
1               5                   10                  15 tct ctg aga ctc tcc tgt gca gcc tct gga ttc acc ttc agt aac tat     96
Ser Leu Arg Leu Ser Cys Ala Ala Ser Gly Phe Thr Phe Ser Asn Tyr
            20                  25                  30

```
gcc atg tac tgg ctc cgc cag gct cca gga aag gga atc gag tgg gtc      144
Ala Met Tyr Trp Leu Arg Gln Ala Pro Gly Lys Gly Ile Glu Trp Val
        35                  40                  45 tcg cgt att ggc cct ggt gga agt cac acc gag tat gca gac tcc gtg      192
Ser Arg Ile Gly Pro Gly Gly Ser His Thr Glu Tyr Ala Asp Ser Val
 50                  55                  60 aag ggc cga ttc acc atc tcc aga gac aac gcc aag aac acg ctg tct      240
Lys Gly Arg Phe Thr Ile Ser Arg Asp Asn Ala Lys Asn Thr Leu Ser
 65                  70                  75                  80 ctg caa atg aac agc ctg aaa cct gag gac acg gcc gtg tat tac tgt      288
Leu Gln Met Asn Ser Leu Lys Pro Glu Asp Thr Ala Val Tyr Tyr Cys
                 85                  90                  95 gcg atc acg caa caa ggt agc ggc cgg ggc cag ggg acc cag gtc acc      336
Ala Ile Thr Gln Gln Gly Ser Gly Arg Gly Gln Gly Thr Gln Val Thr
            100                 105                 110 gtc tcc tca gcg gcc gca ctc gag cac cac cac cac cac cac tga          381
Val Ser Ser Ala Ala Ala Leu Glu His His His His His His
        115                 120                 125
```

<210> SEQ ID NO 11
<211> LENGTH: 126
<212> TYPE: PRT
<213> ORGANISM: Artificial
<220> FEATURE:
<223> OTHER INFORMATION: Synthetic Construct

<400> SEQUENCE: 11

```
Asp Val Gln Leu Gln Val Ser Gly Gly Gly Ser Val Gln Pro Gly Gly
 1               5                  10                  15

Ser Leu Arg Leu Ser Cys Ala Ala Ser Gly Phe Thr Phe Ser Asn Tyr
                20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
 50                  55                  60

Lys Gly Arg Phe Thr Ile Ser Arg Asp Asn Ala Lys Asn Thr Leu Ser
 65                  70                  75                  80

Leu Gln Met Asn Ser Leu Lys Pro Glu Asp Thr Ala Val Tyr Tyr Cys
                 85                  90                  95

Ala Ile Thr Gln Gln Gly Ser Gly Arg Gly Gln Gly Thr Gln Val Thr
            100                 105                 110

Val Ser Ser Ala Ala Ala Leu Glu His His His His His
        115                 120                 125
```

<210> SEQ ID NO 12
<211> LENGTH: 255
<212> TYPE: PRT
<213> ORGANISM: Lama pacos

<400> SEQUENCE: 12

```
Asp Val Gln Leu Gln Val Ser Gly Gly Gly Ser Val Gln Pro Gly Gly
 1               5                  10                  15

Ser Leu Arg Leu Ser Cys Ala Ala Pro Gly Phe Thr Phe Ser Asn Tyr
                20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
 50                  55                  60

Lys Gly Arg Phe Ala Ile Ser Arg Asp Asn Ala Lys Asn Thr Leu Ser
```

```
                65                  70                  75                  80
Leu Gln Met Asn Ser Leu Lys Pro Glu Asp Thr Ala Ala Tyr Tyr Cys
                    85                  90                  95

Ala Ile Thr Gln Gln Gly Ser Gly Arg Gly Arg Gly Thr Gln Val Thr
                100                 105                 110

Val Ser Ser Ala Ala Ala Ser Leu Ser Thr Glu Leu Glu Phe Gly Ser
            115                 120                 125

Glu Leu Ile Pro Ile Ser Met Ala Asp Val Gln Leu Gln Val Ser Gly
        130                 135                 140

Gly Gly Ser Val Gln Pro Gly Gly Ser Leu Arg Leu Ser Cys Ala Ala
145                 150                 155                 160

Ser Gly Phe Thr Phe Ser Asn Tyr Ala Met Tyr Trp Leu Arg Gln Ala
                165                 170                 175

Pro Gly Lys Gly Ile Glu Trp Val Ser Arg Ile Gly Pro Gly Gly Ser
                180                 185                 190

His Thr Glu Tyr Ala Asp Ser Val Lys Gly Arg Phe Thr Ile Ser Arg
            195                 200                 205

Asp Asn Ala Lys Asn Thr Leu Ser Leu Gln Met Asn Ser Leu Lys Pro
        210                 215                 220

Glu Asp Thr Ala Val Tyr Tyr Cys Ala Ile Thr Gln Gln Gly Ser Gly
225                 230                 235                 240

Arg Gly Arg Gly Thr Gln Val Thr Val Ser Ser Ala Ala Ala Ser
                245                 250                 255

<210> SEQ ID NO 13
<211> LENGTH: 789
<212> TYPE: DNA
<213> ORGANISM: Artificial
<220> FEATURE:
<223> OTHER INFORMATION: VHH domain fused to a His tag
<220> FEATURE:
<221> NAME/KEY: CDS
<222> LOCATION: (1)..(789)

<400> SEQUENCE: 13 gat gtc cag ctg cag gtg tct gga gga ggc tcg gtg cag ccg ggg ggg      48
Asp Val Gln Leu Gln Val Ser Gly Gly Gly Ser Val Gln Pro Gly Gly
1               5                   10                  15 tct ctg aga ctc tcc tgt gca gcc cct gga ttc acc ttc agt aac tat      96
Ser Leu Arg Leu Ser Cys Ala Ala Pro Gly Phe Thr Phe Ser Asn Tyr
            20                  25                  30 gcc atg tac tgg ctc cgc cag gct cca gga aag gga atc gag tgg gtc     144
Ala Met Tyr Trp Leu Arg Gln Ala Pro Gly Lys Gly Ile Glu Trp Val
        35                  40                  45 tcg cgt att ggc cct ggt gga agt cac acc gag tac gca gac tcc gtg     192
Ser Arg Ile Gly Pro Gly Gly Ser His Thr Glu Tyr Ala Asp Ser Val
    50                  55                  60 aag ggc cga ttc gcc atc tcc aga gac aac gcc aag aac acg ctg tct     240
Lys Gly Arg Phe Ala Ile Ser Arg Asp Asn Ala Lys Asn Thr Leu Ser
65                  70                  75                  80 ctg caa atg aac agc ctg aaa cct gag gac acg gcg gcg tat tac tgt     288
Leu Gln Met Asn Ser Leu Lys Pro Glu Asp Thr Ala Ala Tyr Tyr Cys
                85                  90                  95 gcg atc acg caa caa ggt agc ggc cgg ggc cgg ggg act caa gtc acc     336
Ala Ile Thr Gln Gln Gly Ser Gly Arg Gly Arg Gly Thr Gln Val Thr
            100                 105                 110 gtc tcc tca gcg gcc gca agc ttg tcg acg gag ctc gaa ttc gga tcc     384
Val Ser Ser Ala Ala Ala Ser Leu Ser Thr Glu Leu Glu Phe Gly Ser
        115                 120                 125
```

```
gaa tta att ccg ata tcc atg gcc gat gtc cag ctg cag gtg tct gga      432
Glu Leu Ile Pro Ile Ser Met Ala Asp Val Gln Leu Gln Val Ser Gly
    130             135                 140 gga ggc tcg gtg cag cct ggg ggg tct ctg aga ctc tcc tgt gca gcc      480
Gly Gly Ser Val Gln Pro Gly Gly Ser Leu Arg Leu Ser Cys Ala Ala
145             150                 155                 160 tct gga ttc acc ttc agt aac tat gcc atg tac tgg ctc cgc cag gct      528
Ser Gly Phe Thr Phe Ser Asn Tyr Ala Met Tyr Trp Leu Arg Gln Ala
                165                 170                 175 cca gga aag gga atc gag tgg gtc tcg cgt att ggc cct ggt gga agt      576
Pro Gly Lys Gly Ile Glu Trp Val Ser Arg Ile Gly Pro Gly Gly Ser
            180                 185                 190 cac acc gag tat gca gac tcc gtg aag ggc cga ttc acc atc tcc aga      624
His Thr Glu Tyr Ala Asp Ser Val Lys Gly Arg Phe Thr Ile Ser Arg
        195                 200                 205 gac aac gcc aag aac acg ctg tct ctg caa atg aac agc ctg aaa cct      672
Asp Asn Ala Lys Asn Thr Leu Ser Leu Gln Met Asn Ser Leu Lys Pro
    210                 215                 220 gag gac acg gcc gtg tat tac tgt gcg atc acg caa caa ggt agc ggc      720
Glu Asp Thr Ala Val Tyr Tyr Cys Ala Ile Thr Gln Gln Gly Ser Gly
225                 230                 235                 240 cgg ggc cgg ggg act caa gtc acc gtc tcc tca gcg gcc gca ctc gag      768
Arg Gly Arg Gly Thr Gln Val Thr Val Ser Ser Ala Ala Ala Leu Glu
                245                 250                 255 cac cac cac cac cac cac tga                                          789
His His His His His His
            260

<210> SEQ ID NO 14
<211> LENGTH: 262
<212> TYPE: PRT
<213> ORGANISM: Artificial
<220> FEATURE:
<223> OTHER INFORMATION: Synthetic Construct

<400> SEQUENCE: 14

Asp Val Gln Leu Gln Val Ser Gly Gly Gly Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala Ser Leu Ser Thr Glu Leu Glu Phe Gly Ser
        115                 120                 125

Glu Leu Ile Pro Ile Ser Met Ala Asp Val Gln Leu Gln Val Ser Gly
    130                 135                 140

Gly Gly Ser Val Gln Pro Gly Gly Ser Leu Arg Leu Ser Cys Ala Ala
145                 150                 155                 160

Ser Gly Phe Thr Phe Ser Asn Tyr Ala Met Tyr Trp Leu Arg Gln Ala
                165                 170                 175
```

Pro Gly Lys Gly Ile Glu Trp Val Ser Arg Ile Gly Pro Gly Gly Ser
            180                 185                 190

His Thr Glu Tyr Ala Asp Ser Val Lys Gly Arg Phe Thr Ile Ser Arg
        195                 200                 205

Asp Asn Ala Lys Asn Thr Leu Ser Leu Gln Met Asn Ser Leu Lys Pro
    210                 215                 220

Glu Asp Thr Ala Val Tyr Tyr Cys Ala Ile Thr Gln Gln Gly Ser Gly
225                 230                 235                 240

Arg Gly Arg Gly Thr Gln Val Thr Val Ser Ser Ala Ala Ala Leu Glu
                245                 250                 255

His His His His His His
            260

<210> SEQ ID NO 15
<211> LENGTH: 8
<212> TYPE: PRT
<213> ORGANISM: Artificial
<220> FEATURE:
<223> OTHER INFORMATION: His tag

<400> SEQUENCE: 15

Leu Glu His His His His His His
1               5

<210> SEQ ID NO 16
<211> LENGTH: 21
<212> TYPE: DNA
<213> ORGANISM: Artificial
<220> FEATURE:
<223> OTHER INFORMATION: Primer

<400> SEQUENCE: 16
cgccatcaag gtaccagttg a                                           21

<210> SEQ ID NO 17
<211> LENGTH: 29
<212> TYPE: DNA
<213> ORGANISM: Artificial
<220> FEATURE:
<223> OTHER INFORMATION: Primer

<400> SEQUENCE: 17
gatgtgcagc tgcaggcgtc tggrggagg                                   29

<210> SEQ ID NO 18
<211> LENGTH: 45
<212> TYPE: DNA
<213> ORGANISM: Artificial
<220> FEATURE:
<223> OTHER INFORMATION: Primer

<400> SEQUENCE: 18
catgccatga ctcgcggccc agccggccat ggccgakgts cagct                 45

<210> SEQ ID NO 19
<211> LENGTH: 35
<212> TYPE: DNA
<213> ORGANISM: Artificial
<220> FEATURE:
<223> OTHER INFORMATION: Primer

<400> SEQUENCE: 19
ggactagttg cggccgctga ggagacggtg acctg                            35

<210> SEQ ID NO 20
<211> LENGTH: 41
<212> TYPE: DNA
<213> ORGANISM: Artificial
<220> FEATURE:
<223> OTHER INFORMATION: Primer

<400> SEQUENCE: 20
ggactagttg cggccgctgg ttgtggtttt ggtgtcttgg g                 41

<210> SEQ ID NO 21
<211> LENGTH: 65
<212> TYPE: DNA
<213> ORGANISM: Artificial
<220> FEATURE:
<223> OTHER INFORMATION: Primer

<400> SEQUENCE: 21
ggagatatat atccatgaga ggatcgcatc accatcacca tcacggatcc gccgakgtsc    60
agctg                                                                65

<210> SEQ ID NO 22
<211> LENGTH: 31
<212> TYPE: DNA
<213> ORGANISM: Artificial
<220> FEATURE:
<223> OTHER INFORMATION: Primer

<400> SEQUENCE: 22
ccatataaag ctttgaggag acggtgacct g                            31

<210> SEQ ID NO 23
<211> LENGTH: 72
<212> TYPE: DNA
<213> ORGANISM: Artificial
<220> FEATURE:
<223> OTHER INFORMATION: Primer

<400> SEQUENCE: 23
agaccacaac ggtttccctc tagaaataat tttgtttaac tttaagaagg agatatatcc    60
atgagaggat cg                                                        72

<210> SEQ ID NO 24
<211> LENGTH: 49
<212> TYPE: DNA
<213> ORGANISM: Artificial
<220> FEATURE:
<223> OTHER INFORMATION: Primer

<400> SEQUENCE: 24
atacgaaatt aatacgactc actataggga gaccacaacg gtttccctc         49

<210> SEQ ID NO 25
<211> LENGTH: 42
<212> TYPE: DNA
<213> ORGANISM: Artificial
<220> FEATURE:
<223> OTHER INFORMATION: Primer

<400> SEQUENCE: 25
caggtcaccg tctcctcaaa gctttatatg gcctcggggg cc                42

<210> SEQ ID NO 26

```
<211> LENGTH: 45
<212> TYPE: DNA
<213> ORGANISM: Artificial
<220> FEATURE:
<223> OTHER INFORMATION: Primer

<400> SEQUENCE: 26
ccgcacacca gtaaggtgtg cggtttcagt tgccgctttc tttct            45

<210> SEQ ID NO 27
<211> LENGTH: 41
<212> TYPE: DNA
<213> ORGANISM: Artificial
<220> FEATURE:
<223> OTHER INFORMATION: Primer

<400> SEQUENCE: 27
atacgaaatt aatacgactc actatagggA gaccacaacg g                41

<210> SEQ ID NO 28
<211> LENGTH: 711
<212> TYPE: DNA
<213> ORGANISM: Artificial
<220> FEATURE:
<223> OTHER INFORMATION: VHH domain fused in frame with the Ig CH2
      domain and a His tag
<220> FEATURE:
<221> NAME/KEY: CDS
<222> LOCATION: (1)..(711)

<400> SEQUENCE: 28
```

| gat | gtc | cag | ctg | cgg | gcg | tct | gga | gga | ggc | tta | gtg | cag | cct | ggg | ggg |  48 |
|---|---|---|---|---|---|---|---|---|---|---|---|---|---|---|---|---|
| Asp | Val | Gln | Leu | Arg | Ala | Ser | Gly | Gly | Gly | Leu | Val | Gln | Pro | Gly | Gly |  |
| 1 | | | | 5 | | | | | 10 | | | | | 15 | | |

| tct | ctg | aga | ctc | tcc | tgt | gca | gcc | tct | gga | ttc | acc | ttc | agt | aac | tat |  96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Asn | Tyr |  |
| | | 20 | | | | | 25 | | | | | 30 | | | | |

| gcc | atg | tac | tgg | ctc | cgc | cag | gct | cca | gga | aag | gga | atc | gag | tgg | gtc | 144 |
|---|---|---|---|---|---|---|---|---|---|---|---|---|---|---|---|---|
| Ala | Met | Tyr | Trp | Leu | Arg | Gln | Ala | Pro | Gly | Lys | Gly | Ile | Glu | Trp | Val |  |
| | | 35 | | | | 40 | | | | | 45 | | | | | |

| tcg | cgt | att | ggc | cct | ggt | gga | agt | cac | acc | gag | tat | gca | gac | tcc | gtg | 192 |
|---|---|---|---|---|---|---|---|---|---|---|---|---|---|---|---|---|
| Ser | Arg | Ile | Gly | Pro | Gly | Gly | Ser | His | Thr | Glu | Tyr | Ala | Asp | Ser | Val |  |
| 50 | | | | | 55 | | | | | 60 | | | | | | |

| aag | ggc | cga | ttc | acc | atc | tcc | aga | gac | aac | gcc | aag | aac | acg | ctg | tct | 240 |
|---|---|---|---|---|---|---|---|---|---|---|---|---|---|---|---|---|
| Lys | Gly | Arg | Phe | Thr | Ile | Ser | Arg | Asp | Asn | Ala | Lys | Asn | Thr | Leu | Ser |  |
| 65 | | | | 70 | | | | | 75 | | | | | 80 | | |

| ctg | caa | atg | aac | agc | ctg | aaa | cct | gag | gac | acg | gcc | gtg | tat | tac | tgt | 288 |
|---|---|---|---|---|---|---|---|---|---|---|---|---|---|---|---|---|
| Leu | Gln | Met | Asn | Ser | Leu | Lys | Pro | Glu | Asp | Thr | Ala | Val | Tyr | Tyr | Cys |  |
| | | | | 85 | | | | | 90 | | | | | 95 | | |

| gcg | atc | acg | caa | caa | ggt | agc | ggc | cgg | ggc | cag | gag | acc | cag | gtc | acc | 336 |
|---|---|---|---|---|---|---|---|---|---|---|---|---|---|---|---|---|
| Ala | Ile | Thr | Gln | Gln | Gly | Ser | Gly | Arg | Gly | Gln | Glu | Thr | Gln | Val | Thr |  |
| | | | 100 | | | | | 105 | | | | | 110 | | | |

| gtc | tcc | tca | gcg | gcc | gca | gcc | cct | gag | ctc | ctg | gga | ggg | ccc | tca | gtc | 384 |
|---|---|---|---|---|---|---|---|---|---|---|---|---|---|---|---|---|
| Val | Ser | Ser | Ala | Ala | Ala | Ala | Pro | Glu | Leu | Leu | Gly | Gly | Pro | Ser | Val |  |
| | | 115 | | | | | 120 | | | | | 125 | | | | |

| ttc | atc | ttc | ccc | ccg | aaa | ccc | aag | gac | gtc | ctc | tcc | att | tct | ggg | agg | 432 |
|---|---|---|---|---|---|---|---|---|---|---|---|---|---|---|---|---|
| Phe | Ile | Phe | Pro | Pro | Lys | Pro | Lys | Asp | Val | Leu | Ser | Ile | Ser | Gly | Arg |  |
| | | 130 | | | | | 135 | | | | | 140 | | | | |

| ccc | gag | gtc | acg | tgc | gtt | gtg | gta | gac | gtg | ggc | cag | gaa | gac | ccc | gag | 480 |
|---|---|---|---|---|---|---|---|---|---|---|---|---|---|---|---|---|
| Pro | Glu | Val | Thr | Cys | Val | Val | Val | Asp | Val | Gly | Gln | Glu | Asp | Pro | Glu |  |
| 145 | | | | 150 | | | | | 155 | | | | | 160 | | |

| gtc | agt | ttc | aac | tgg | tac | att | gat | ggc | gct | gag | gtg | cga | acg | gcc | aac | 528 |
|---|---|---|---|---|---|---|---|---|---|---|---|---|---|---|---|---|
| Val | Ser | Phe | Asn | Trp | Tyr | Ile | Asp | Gly | Ala | Glu | Val | Arg | Thr | Ala | Asn |  |
| | | | | 165 | | | | | 170 | | | | | 175 | | |

```
acg agg cca aaa gag gaa cag ttc aac agc acg tac cgc gtg gtc agc      576
Thr Arg Pro Lys Glu Glu Gln Phe Asn Ser Thr Tyr Arg Val Val Ser
        180                 185                 190 gtc ctg ccc atc cag cac cag gac tgg ctg acg ggg aag gaa ttc aag      624
Val Leu Pro Ile Gln His Gln Asp Trp Leu Thr Gly Lys Glu Phe Lys
        195                 200                 205 tgc aag gtc aac aac aaa gct ctc ccg gcc ccc atc gag aag acc atc      672
Cys Lys Val Asn Asn Lys Ala Leu Pro Ala Pro Ile Glu Lys Thr Ile
        210                 215                 220 tcc aag gcc aaa ctc gag cac cac cac cac cac cac tga                  711
Ser Lys Ala Lys Leu Glu His His His His His His
225                 230                 235
```

<210> SEQ ID NO 29
<211> LENGTH: 236
<212> TYPE: PRT
<213> ORGANISM: Artificial
<220> FEATURE:
<223> OTHER INFORMATION: Synthetic Construct

<400> SEQUENCE: 29

```
Asp Val Gln Leu Arg Ala Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95

Ala Ile Thr Gln Gln Gly Ser Gly Arg Gly Gln Glu Thr Gln Val Thr
            100                 105                 110

Val Ser Ser Ala Ala Ala Ala Pro Glu Leu Leu Gly Gly Pro Ser Val
        115                 120                 125

Phe Ile Phe Pro Pro Lys Pro Lys Asp Val Leu Ser Ile Ser Gly Arg
    130                 135                 140

Pro Glu Val Thr Cys Val Val Val Asp Val Gly Gln Glu Asp Pro Glu
145                 150                 155                 160

Val Ser Phe Asn Trp Tyr Ile Asp Gly Ala Glu Val Arg Thr Ala Asn
                165                 170                 175

Thr Arg Pro Lys Glu Glu Gln Phe Asn Ser Thr Tyr Arg Val Val Ser
            180                 185                 190

Val Leu Pro Ile Gln His Gln Asp Trp Leu Thr Gly Lys Glu Phe Lys
        195                 200                 205

Cys Lys Val Asn Asn Lys Ala Leu Pro Ala Pro Ile Glu Lys Thr Ile
    210                 215                 220

Ser Lys Ala Lys Leu Glu His His His His His
225                 230                 235
```

<210> SEQ ID NO 30
<211> LENGTH: 32
<212> TYPE: DNA
<213> ORGANISM: Artificial
<220> FEATURE:
<223> OTHER INFORMATION: Primer -continued

```
<400> SEQUENCE: 30
gggtctctga gactctcctc tgcagcctct gg                                        32

<210> SEQ ID NO 31
<211> LENGTH: 26
<212> TYPE: DNA
<213> ORGANISM: Artificial
<220> FEATURE:
<223> OTHER INFORMATION: Primer

<400> SEQUENCE: 31
ccagaggctg cagaggagag tctcag                                               26

<210> SEQ ID NO 32
<211> LENGTH: 38
<212> TYPE: DNA
<213> ORGANISM: Artificial
<220> FEATURE:
<223> OTHER INFORMATION: Primer

<400> SEQUENCE: 32
ctaccttgtt gcgtgatcgc agagtaatac acggccgt                                  38

<210> SEQ ID NO 33
<211> LENGTH: 39
<212> TYPE: DNA
<213> ORGANISM: Artificial
<220> FEATURE:
<223> OTHER INFORMATION: Primer

<400> SEQUENCE: 33
acggccgtgt attactctgc gatcacgcaa caaggtagc                                 39
```